(12) United States Patent
Pressly et al.

(10) Patent No.: US 10,792,233 B2
(45) Date of Patent: *Oct. 6, 2020

(54) METHODS AND FORMULATIONS FOR CURLING HAIR

(71) Applicant: Olaplex, Inc., Boston, MA (US)

(72) Inventors: Eric D. Pressly, Santa Barbara, CA (US); Craig J. Hawker, Santa Barbara, CA (US)

(73) Assignee: OLAPLEX, INC., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/855,719

(22) Filed: Dec. 27, 2017

(65) Prior Publication Data

US 2018/0116931 A1    May 3, 2018

Related U.S. Application Data

(63) Continuation of application No. 15/640,044, filed on Jun. 30, 2017, now Pat. No. 9,872,821, which is a continuation-in-part of application No. 15/282,795, filed on Sep. 30, 2016, now Pat. No. 9,713,583.

(60) Provisional application No. 62/380,020, filed on Aug. 26, 2016, provisional application No. 62/361,366, filed on Jul. 12, 2016.

(51) Int. Cl.
| | | |
|---|---|---|
| A61K 8/41 | (2006.01) | |
| A61Q 5/04 | (2006.01) | |
| A61K 8/46 | (2006.01) | |
| A61K 8/36 | (2006.01) | |
| A45D 7/04 | (2006.01) | |
| A61K 8/19 | (2006.01) | |
| A61K 8/362 | (2006.01) | |
| A61Q 5/06 | (2006.01) | |

(52) U.S. Cl.
CPC .................. *A61K 8/41* (2013.01); *A45D 7/04* (2013.01); *A61K 8/19* (2013.01); *A61K 8/36* (2013.01); *A61K 8/362* (2013.01); *A61K 8/466* (2013.01); *A61Q 5/04* (2013.01); *A61Q 5/06* (2013.01); *A61K 2800/30* (2013.01); *A61K 2800/882* (2013.01)

(58) Field of Classification Search
None
See application file for complete search history.

(56) References Cited

U.S. PATENT DOCUMENTS

| | | | |
|---|---|---|---|
| 2,850,351 A | 9/1958 | Moore | |
| 3,142,623 A | 7/1964 | Zviak | |
| 3,472,243 A | 10/1969 | Wall | |
| 3,568,685 A * | 3/1971 | Scott | A61K 8/19 |
| | | | 132/206 |
| 3,840,656 A | 10/1974 | Kalopissis | |
| 4,067,345 A | 1/1978 | Kelly | |
| 4,138,478 A | 2/1979 | Reese | |
| 4,240,450 A | 12/1980 | Grollier | |
| 4,425,132 A | 1/1984 | Grollier | |
| 4,532,950 A | 8/1985 | Lang | |
| 4,567,039 A | 1/1986 | Stadnick | |
| 4,793,993 A | 12/1988 | Siuta-Mangano | |
| 4,812,307 A | 3/1989 | Siuta-Mangano | |
| 4,834,971 A | 5/1989 | Klenk | |
| 5,143,518 A | 9/1992 | Madrange | |
| 5,221,286 A | 6/1993 | Singleton | |
| 5,350,572 A | 9/1994 | Savaides | |
| 5,356,438 A | 10/1994 | Kim | |
| 5,565,216 A | 10/1996 | Cowsar | |
| 5,651,960 A | 7/1997 | Chan | |
| 5,656,265 A | 8/1997 | Bailey | |
| 5,811,085 A | 9/1998 | Halloran | |
| 5,833,966 A | 11/1998 | Samain | |
| 6,010,690 A | 1/2000 | Varco | |
| 6,173,717 B1 | 1/2001 | Schonert | |
| 6,358,502 B1 | 3/2002 | Tanabe | |
| 6,458,906 B1 | 10/2002 | Torgerson | |
| 6,537,532 B1 | 3/2003 | Torgerson | |
| 6,706,258 B1 | 3/2004 | Gallagher | |
| 6,984,250 B1 | 1/2006 | Legrand | |
| 7,041,142 B2 | 5/2006 | Chan | |
| 7,044,986 B2 | 5/2006 | Ogawa | |
| 7,179,302 B2 | 2/2007 | Baswell | |
| 7,390,479 B2 | 6/2008 | Sockel | |
| 7,597,880 B2 | 10/2009 | Darkwa | |
| 7,598,213 B2 | 10/2009 | Geary | |
| 8,137,414 B2 * | 3/2012 | Wood | A61K 8/41 |
| | | | 8/405 |
| 8,298,519 B2 | 10/2012 | Adams | |

(Continued)

FOREIGN PATENT DOCUMENTS

| | | |
|---|---|---|
| DE | 1220969 | 7/1966 |
| DE | 4300320 | 7/1994 |

(Continued)

OTHER PUBLICATIONS

Relaxing agents, Milday Standard Cosmetology, 13th edition, 2016, pp. 618-625.*

(Continued)

*Primary Examiner* — Abigail Vanhorn
(74) *Attorney, Agent, or Firm* — Pabst Patent Group LLP

(57) ABSTRACT

Methods, formulations, and kits for curling and/or preventing damage in the curling of hair are disclosed herein. Hair can be curled by treatment with hydroxide-containing agents, in combination with one or more active agents, without the need for thiol-based or peroxide-based agents. The active agent can be applied simultaneously with the hydroxide-containing agent, to impart curl to the hair. They may be applied as a combined formulation or as separate formulations applied simultaneously. Use of the active agent along with a hydroxide-containing agent can be used to control the level of curl imparted to hair, as compared to the natural amount of curl, if any, in the untreated hair.

22 Claims, No Drawings

(56) References Cited

U.S. PATENT DOCUMENTS

| | | | |
|---|---|---|---|
| 8,556,992 | B2 | 10/2013 | De George |
| 8,613,913 | B2 | 12/2013 | Chang |
| 9,055,518 | B2 | 6/2015 | Vainola |
| 9,095,518 | B2 | 8/2015 | Pressly |
| 9,144,537 | B1 | 9/2015 | Pressly |
| 9,180,086 | B2 | 11/2015 | Cabourg |
| 9,326,926 | B2 | 5/2016 | Pressly |
| 9,498,419 | B2 | 11/2016 | Pressly |
| 9,597,273 | B2 * | 3/2017 | Pressly ............ A45D 7/00 |
| 9,668,954 | B2 | 6/2017 | Pressly |
| 9,713,583 | B1 * | 7/2017 | Pressly ............ A61K 8/19 |
| 9,717,668 | B2 | 8/2017 | Pressly |
| 9,855,447 | B2 | 1/2018 | Pressly |
| 9,872,821 | B1 * | 1/2018 | Pressly ............ A61K 8/466 |
| 10,076,475 | B2 | 9/2018 | Gershon |
| 10,076,478 | B2 | 9/2018 | Pressly |
| 10,376,457 | B2 * | 8/2019 | Baum ............ A61K 8/36 |
| 2001/0042276 | A1 | 11/2001 | Kawasoe |
| 2002/0189034 | A1 | 12/2002 | Kitabata |
| 2003/0037384 | A1 | 2/2003 | Nguyen |
| 2003/0049222 | A1 | 3/2003 | Akhter |
| 2003/0072962 | A1 | 4/2003 | Matsuzaki |
| 2004/0034944 | A1 | 2/2004 | Legrand |
| 2004/0034946 | A1 | 2/2004 | Legrand |
| 2004/0086475 | A1 | 5/2004 | Boswell |
| 2004/0088800 | A1 | 5/2004 | Cotteret |
| 2005/0036970 | A1 | 2/2005 | Sabbagh |
| 2005/0087718 | A1 | 4/2005 | Okada |
| 2006/0024257 | A1 | 2/2006 | Chang |
| 2006/0228316 | A1 | 10/2006 | Cannell |
| 2007/0041921 | A1 | 2/2007 | Neill |
| 2007/0067924 | A1 | 3/2007 | Beck |
| 2007/0141005 | A1 * | 6/2007 | Wood ............ A61K 8/355 424/70.2 |
| 2007/0261594 | A1 | 11/2007 | Vaskelis |
| 2007/0264208 | A1 | 11/2007 | Mougin |
| 2008/0066773 | A1 | 3/2008 | Anderson |
| 2008/0138309 | A1 | 6/2008 | Malle |
| 2008/0141468 | A1 | 6/2008 | Cotteret |
| 2008/0187506 | A1 | 8/2008 | Carballada |
| 2009/0022681 | A1 | 1/2009 | Carballada |
| 2009/0126756 | A1 | 5/2009 | Syed |
| 2009/0252697 | A1 | 10/2009 | Barbarat |
| 2010/0004391 | A1 | 1/2010 | Haddleton |
| 2010/0015253 | A1 | 1/2010 | Benjamin |
| 2010/0202998 | A1 | 8/2010 | Ramos-Stanbury |
| 2011/0038818 | A1 | 2/2011 | Onyebuagu |
| 2011/0250153 | A1 | 10/2011 | Owen |
| 2011/0256084 | A1 | 10/2011 | Dixon |
| 2012/0024309 | A1 | 2/2012 | Pratt |
| 2012/0114584 | A1 | 5/2012 | Woghiren |
| 2012/0180807 | A1 | 7/2012 | Flohr |
| 2012/0244082 | A1 | 9/2012 | Sulzbach |
| 2013/0034515 | A1 | 2/2013 | Stone |
| 2013/0152959 | A1 | 6/2013 | Genain |
| 2013/0172518 | A1 | 7/2013 | Huang |
| 2013/0309190 | A1 | 11/2013 | Dimotakis |
| 2014/0125452 | A1 | 5/2014 | Josefiak |
| 2014/0186283 | A1 | 7/2014 | Cabourg |
| 2014/0196741 | A1 | 7/2014 | Cabourg |
| 2015/0034117 | A1 | 2/2015 | Pressly |
| 2015/0034119 | A1 | 2/2015 | Pressly |
| 2015/0297496 | A1 | 10/2015 | Kroon |
| 2015/0328102 | A1 | 11/2015 | Pressly |
| 2016/0081899 | A1 | 3/2016 | Pressly |
| 2016/0193129 | A1 | 7/2016 | Pressly |
| 2016/0263003 | A1 | 9/2016 | Pressly |
| 2016/0310394 | A1 * | 10/2016 | Pressly ............ A61K 8/466 |

FOREIGN PATENT DOCUMENTS

| | | |
|---|---|---|
| DE | 10051773 | 4/2002 |
| DE | 10051774 | 4/2002 |
| DE | 102004052480 | 5/2006 |
| DE | 202015104742 | 10/2015 |
| EC | 993171 | 10/1999 |
| EC | 055712 | 3/2005 |
| EP | 0299764 | 1/1989 |
| EP | 0298684 | 4/1993 |
| EP | 0609796 | 8/1994 |
| EP | 0978272 | 2/2000 |
| EP | 1174112 | 1/2002 |
| EP | 1726289 | 11/2006 |
| EP | 1779896 | 5/2007 |
| EP | 2295029 | 3/2011 |
| EP | 2478892 | 7/2012 |
| FR | 1356138 | 3/1964 |
| FR | 1356139 | 3/1964 |
| FR | 2975900 | 12/2012 |
| GB | 713675 | 8/1954 |
| GB | 741307 | 11/1955 |
| GB | 773559 | 4/1957 |
| GB | 1125794 | 8/1968 |
| GB | 1260451 | 1/1972 |
| GB | 1584364 | 2/1981 |
| JP | 02138110 | 5/1990 |
| JP | H02138110 | 5/1990 |
| JP | 2006327994 | 12/2006 |
| JP | 2009007283 | 1/2009 |
| JP | 2010155823 | 7/2010 |
| KR | 830002888 | 12/1983 |
| KR | 830002888 B1 * | 12/1983 |
| KR | 20010039848 | 7/2001 |
| KR | 1020030003970 | 1/2003 |
| KR | 20040098688 | 11/2004 |
| KR | 1020060059564 | 6/2006 |
| WO | 9300882 | 1/1993 |
| WO | 9308787 | 5/1993 |
| WO | 9501152 | 1/1995 |
| WO | 1997024106 | 7/1997 |
| WO | 2001047486 | 7/2001 |
| WO | 0232383 | 4/2002 |
| WO | 0232386 | 4/2002 |
| WO | 2002032383 | 4/2002 |
| WO | 2002032386 | 4/2002 |
| WO | 02074272 | 9/2002 |
| WO | 2006011771 | 2/2006 |
| WO | 2009024936 | 2/2006 |
| WO | 2006051287 | 5/2006 |
| WO | 2008072672 | 6/2008 |
| WO | 2010049434 | 5/2010 |
| WO | 2011134785 | 11/2011 |
| WO | 2012084532 | 1/2012 |
| WO | 2012164064 | 1/2012 |
| WO | 2012080321 | 6/2012 |
| WO | 2012122457 | 9/2012 |
| WO | WO-2012164064 A1 * | 12/2012 ............ A61K 8/362 |
| WO | 2014016407 | 1/2014 |
| WO | 2014118212 | 8/2014 |
| WO | 2014125452 | 8/2014 |
| WO | 2014167508 | 10/2014 |
| WO | 2014207097 | 12/2014 |
| WO | 2015017768 | 2/2015 |
| WO | 2015026994 | 2/2015 |
| WO | 2015175986 | 11/2015 |
| WO | 2016207840 | 12/2016 |
| WO | 2017041908 | 3/2017 |

OTHER PUBLICATIONS

Amended Statement of Case on Validity (Olaplex) Redacted Version filed Nov. 6, 2017.
Barradas, et al., "The hydrolysis of maleimide in alkaline solution", Can. J. Chem, 54, 1400-1404 (1976).
Borish, Desposition transcript, pp. 1-204, Jan. 5, 2018.
Borish, Edward T.—Declaration, signed Oct. 18, 2017 (Redacted, non-confidential version).
Borish, Edwart T.—CV.
Bouillon and Wilkinson, Chapter 1, "Hair Structure, Function, and Physicochemical Properties" in The Science of Hair Care, (2005).
Bouillon and Wilkinson, Chapter 12, "Hair Structure, Function, and Physicochemical Properties" in The Science of Hair Care, (2005).

(56) References Cited

OTHER PUBLICATIONS

Brown and Pohl, "Permanent Hair Dyes" in Society of Cosmetic Chemists.
Brown Keith C. (1997) Hair Coloring, Clairol, Inc., Stamford, Connecticut.
Catzy Blonde translation.
Chromastics, "The evolution of hair color", Technical ad training manual, pp. 1-32 (2009).
CIR Safety Report "Final Report on the Safety Assessment of Maleic Acid", International Journal of Toxicology, 26 (Suppl.2); 125-131, (2007).
Clairol Professional Basic White powder lightener label with instructions and ingredients.
CTFA Cosmetic Ingredient handbook, pp. 1023-1 thru 1023-8, John Wenninger Editor, (1992).
Dispenza License status webpage, https://aca.licensecenter.ny.gov/aca/GeneralProperty/LicenseeDetail, retrieved from the internet Dec. 12, 2017.
Dispenza, Thomas—Deposition transcript, pp. 1-125, Dec. 13, 2017.
E-mail correspondence regarding documentary evidence as provided by the third party (Ex 36).
English Translation of Packaging in Mintel Database, Record ID 743114, Catzy Hair Colourant, Published Jul. 2007.
Evans , "Fatigue testing of hair—A statistical approach to hair breakage", J Cosmet. Sci., 60:599-616 (2009).
Ex 1048—Public Version of Exhibit 1036, Laboratory Notebook.
Ex 2003—*Liqwd* V. *L'Oreal* 2018 WL480759 (Fed.Cir 2018).
Ex 2004—Trial Testimony in *Liqwd, Inc. et al. V. L'Oreal (UK) Ltd. et al.*, EQHC Patents Court, Claim No. HP-2016-000056, Apr. 26, 2018.
Ex 2034—Felthouse et al, "Maleic Anhydride, Maleic Acid, and Fumaric Acid"—Kirk-Othmer Encyclopedia of Chemical Technology (First Published Oct. 18, 2001).
Ex 2036—Maleic Acid Safety Data Sheet Vertellus 2011.
Ex 2043—Excerpt From Youtube Video Entitled "How Does Smartbond Technology Work?" by L'Oreal Professionnel, Available at https://youtu.be/lmyb5fiel1g?t=31 (Visited Oct. 18, 2018).
Ex 2044—Redken Ph-Bonder Technical Guide—Aug. 2016.
Ex 2045—Matrix Bond ULTIM8 Techniques Guide.
Ex 2047—Matrix Bond ULTIM8 Bottle Instructions.
Ex 2048—Matrix Bond ULTIM8 Package Instructions.
Ex 2049—Lab Report From Analyze, Inc.
Ex 2050—Redken PH-Bonder Bottle Instructions.
Ex 2051—Redken PH-Bonder Package Instructions.
Ex 2052—L'Oreal Professionnel Smartbond Bottle Instructions.
Ex 2053—L'Oreal Professionnel Smartbond Package Instructions.
Ex 2055—Wolfram, "The Reactivity of Human Hair. A Review" Hair Research, 1981.
Ex 2056—Dubief et al., Chpt 4 "Hair Care Products" From The Science of Hair Care (Bouillon C, Wilkinson, J. Eds.), 2d Edn. 2005.
Ex 2058—Types of Professional Haircolor Services (Redken), https:www.redken.com/haircolor/types-of-professional-haircolor-services (Obtained Jun. 2, 2018).
Ex 2060—Corbett, "The Chemistry of Hair-Care Products" J. Soc'y of Dyers and Colourists 92(8):285-303, 1976.
Ex 2063—Harris, Chpt 9, "Monoprotic Acid-Base Equilibira" From The Science of Hair Care (Bouillon C, Wilkinson j, Eds., 2d Edn., 2005.
Ex 2066—Harris, Chpt 10, "Polyprotic Acid-Base Equilibria" From Quantitative Chemical Analysis, 7th Ed., 2007.
Ex 2073—(PGR 2018-00025)—Redacted Declaration of Dean Christal, Dated Oct. 31, 2018.
Ex 2074—(PGR 2018-00025)—Redacted Declaration of Edward T. Borish, PhD Dated Nov. 16, 2018.
Ex 2075—(PGR 2018-00025)—Redacted—Liqwd Inc's Patent Owner Response Under 37 C.F.R. 42.220.
FMC Webinar—The Science of Persulfate Activation, Apr. 24, 2013.
Haddleton CV Jan. 2, 2018.
Haddleton report dated Feb. 2, 2018 (Redacted).
Haddleton report dated Mar. 29, 2018 (Redacted).
Haddleton report, dated Apr. 24, 2018.
Hefferd, Robert—Declaration—Redacted version—Part 1of3; with Appendices (1-3) and Exhibits (A-O), filed in *Liqwd, Inc. et al.* v. *L'Oréal USA, Inc. et al.*, U.S. District Court for the District of Delaware, Civil Action No. 1:17-cv-00014 on Apr. 17, 2017.
Hefferd, Robert—Declaration—Redacted version—Part 2of3; with Appendices (1-3) and Exhibits (A-O), filed in *Liqwd, Inc. et al.* v. *L'Oréal USA, Inc. et al.*, U.S. District Court for the District of Delaware, Civil Action No. 1:17-cv-00014 on Apr. 17, 2017.
Hefferd, Robert—Declaration—Redacted version—Part 3of3; with Appendices (1-3) and Exhibits (A-O), filed in *Liqwd, Inc. et al.* v. *L'Oréal USA, Inc. et al.*, U.S. District Court for the District of Delaware, Civil Action No. 1:17-cv-00014 on Apr. 17, 2017.
Hefford, Robert—report, dated Apr. 25, 2018.
Hefford, Robert—report, dated Feb. 2, 2018.
Hefford, Robert—report, dated Mar. 29, 2018.
INCI Listing "Ingredient: Bis-Aminopropyl Diglycol Dimaleate" Cosmetics—Cosing [EC Regulation (v.2)].
Joico Bleach Powder label with instructions and ingredients.
Joico Verolight Dust-Free Lightening Powder (Sleek Shop).
Kamath and Robbins, "Hair breakage by combing and brushing—A comment on: T.A. Evans and K. Park, A statistical analysis of hair breakage. II Repeated grooming experiments", J. Cosmet. Sci., 41:439-56 (2010).
KR 20030003970—Certified English Tranlsation Jan. 14, 2003 LG Household & Health Care, Ltd.
KR 2003003970—English Translation Jan. 14, 2003 LG Household & Health Care, Ltd.
L'Oreal Invalidity Opinion Ex A01.
L'Oreal Invalidity Opinion Ex A02.
L'Oreal Invalidity Opinion Ex A03.
L'Oreal Invalidity Opinion Ex A04.
L'Oreal Invalidity Opinion Ex A05.
L'Oreal Invalidity Opinion Ex A06.
L'Oreal Invalidity Opinion Ex A07.
L'Oreal Invalidity Opinion Ex A08.
L'Oreal Invalidity Opinion Ex A09.
L'Oreal Invalidity Opinion Ex A10.
L'Oreal Invalidity Opinion Ex A11.
L'Oreal Invalidity Opinion Ex A12.
L'Oreal Invalidity Opinion Ex A13.
L'Oreal Invalidity Opinion Ex A14.
L'Oreal Invalidity Opinion Ex A15.
L'Oreal Invalidity Opinion Ex A16.
L'Oreal Invalidity Opinion Ex A17.
L'Oreal Invalidity Opinion Ex A18.
L'Oreal Invalidity Opinion Ex A19.
L'Oreal Invalidity Opinion Ex A20.
L'Oreal Invalidity Opinion Ex A21.
L'Oreal Invalidity Opinion Ex A22.
L'Oreal Invalidity Opinion Ex A23.
L'Oreal Invalidity Opinion Ex A24.
L'Oreal Invalidity Opinion Ex A25.
L'Oreal Invalidity Opinion Ex A26.
L'Oreal Invalidity Opinion Ex A27.
L'Oreal Invalidity Opinion Ex A28.
L'Oreal Invalidity Opinion Ex A29.
L'Oreal Invalidity Opinion Ex A30.
L'Oreal Invalidity Opinion Ex A31.
L'Oreal Invalidity Opinion Ex A32.
L'Oreal Invalidity Opinion Ex A33.
L'Oreal Invalidity Opinion Ex A34.
L'Oreal Invalidity Opinion Ex A35.
L'Oreal Invalidity Opinion Ex A36.
L'Oreal Invalidity Opinion Ex A37.
L'Oreal Invalidity Opinion Ex A38.
L'Oreal Invalidity Opinion Ex A39.
L'Oreal Invalidity Opinion Ex A40.
L'Oreal Invalidity Opinion Ex A41.
L'Oreal Invalidity Opinion Ex A42.
L'Oreal Invalidity Opinion Ex A43.

(56) References Cited

OTHER PUBLICATIONS

L'Oreal Invalidity Opinion Ex A44.
L'Oreal Invalidity Opinion Ex A45.
L'Oreal Invalidity Opinion Ex A46.
L'Oreal Invalidity Opinion Ex A47.
L'Oreal Quick Blue Bleach Powder Label and Instructions.
Law, Robert—Declaration dated Jul. 13, 2018, Filed by L'Oreal in GB 1605346.4 and GB 1813313.2.
Matrix Light Master Bleach Powder Label and Instructions.
Memorandum filed in response to official action dated Jun. 5, 2017 in corresponding Israel application No. 248989.
Nandagiri, Arun—Declaration signed Jan. 30, 2017 (Ex.1008) with CV (Ex.1016).
Nandagiri, Arun—Deposition transcript dated Mar. 2, 2018 (Ex 2055).
Nandagiri, Arun—Deposition transcript dated Mar. 14, 2018 (Ex 2057).
Nandagiri, Arun—Deposition transcript dated Oct. 6, 2017.
Nandagiri, Arun—Rebuttal Declaration dated Jan. 26, 2018 (Ex 1040).
Nandagiri, Arun—Rebuttal Declaration, pp. 1-7, Jan. 30, 2017.
Office Action for CA (Canada) 2947303—dated Sep. 17, 2018.
Office Action for CA (Canada) 2947303, dated Oct. 10, 2018.
Office Action for CA (Canada) CA 2,947,303 dated Dec. 21, 2017.
Office Action for CL (Chile) 201600158 dated Jun. 18, 2018, with English Summary.
Office Action for CL (Chile) 201602911—dated Sep. 27, 2018, with English Summary.
Office Action for CL (Chile) 201602911 dated Apr. 11, 2018, with English Translation.
Office Action for CN (China) 201480042200.1 dated Jan. 1, 2018.
Office Action for CN (China) 201480042200.10 dated Aug. 3, 2018 with English Summary.
Office Action for CN (China) 201480042200.10, dated Nov. 9, 2018, with English Summary.
Office Action for CN (China) 201580026038.9—dated Sep. 5, 2018 with English Summary.
Office Action for CN (China) 201580026038.90 dated Dec. 18, 2017, with English Summary.
Office Action for CU (Cuba) 2016-0017 dated Jan. 26, 2018.
Office Action for CU (Cuban) 2016-0017 dated Jun. 20, 2018 (English Translation).
Office Action for DO (Dominican Republic) P20160030 dated Apr. 10, 2018 (English Summary).
Office Action for DO (Dominican Republic) P20160030, dated Sep. 18, 2018, with English Summary.
Office Action for EA (Eurasia) 201592291 dated May 8, 2018, with English Translation.
Office Action for EA (Eurasia) 201592291, dated Aug. 30, 2018, with English Summary.
Office Action for EA (Eurasia) 201692315 dated May 17, 2018 , with English Translation.
Office Action for EA (Eurasia)201592291 dated Aug. 1, 2017.
Office Action for EG (Egypt) 2016111820, dated Nov. 26, 2018, with English Translation.
Office Action for EP (Europe) 15725209.9 dated Jan. 1, 2018.
Office Action for EP (Europe) 17163334.0 dated Apr. 26, 2018.
Office Action for EP (Europe)15725209.9, dated May 18, 2017.
Office Action for EP 15725209.9, dated Aug. 15, 2018.
Office Action for GB (United Kingdom) 1813313.2, dated Sep. 20, 2018.
Office Action for HN (Honduras) 2016-000236 dated Feb. 1, 2019 with English Translation.
Office Action for ID (Indonesia) P00201600646 dated May 25, 2018,with English Translation.
Office Action for IL (Israel) 248989, dated Oct. 7, 2018 with English Summary.
Office Action for IL (Israel) 248989 (with third party submission) dated Sep. 6, 2017 (English Summary).
Office Action for IL (Israel) 248989 dated Mar. 4, 2018.

Office Action for IN (India) 20147007019.00, dated Sep. 6, 2018, with English Translation.
Office Action for IN (India) 201617038524, dated May 12, 2018, with English Translation.
Office Action for JP (Japan) 2016-572832, dated Oct. 26 2017 (English Translation).
Office Action for JP (Japan) 2016-515948, dated Oct. 3, 2017.
Office Action for JP (Japan) 2016-572832, dated Aug. 2, 2018, with English Translation.
Office Action for JP (Japan) 2016-572832, dated Jul. 31, 2018, English Translation.
Office Action for JP (Japan) 2016515948, dated Jun. 27, 2017, English Tranlsation.
Office Action for KR (Republic of Korea) 10-2016-7034158, dated May 18, 2018, with English Translation.
Office Action for MX (Mexico) MX/a/2016/014917, dated Dec. 7, 2018, with English Summary.
Office Action for MX (Mexico) MX/a/2016/014917, dated Jun. 20, 2018.
Office Action for MX (Mexico) MXa/2016/00176 dated Aug. 24, 2017.
Office Action for NZ (New Zealand) 725652, dated May 22, 2018 (Examination Report).
Office Action for SA (Saudi Arabia) 516370509, dated Aug. 1, 2017 with English Summary.
Office Action for SG (Singapore) 11201609005Q, dated May 24, 2017.
Office Action for SG (Singapore) 11201609005Q, dated Nov. 29, 2017.
Office Action for SG (Singapore) 11201609005Q, dated Sep. 28, 2018.
Office Action for SV (El Salvador) 20160019660, dated Mar. 14, 2018, with English Translation.
Office Action for SV (El Salvador) 2016005320, dated Oct. 5, 2018.
Office Action for U.S. Appl. No. 14/713,885, dated Aug. 17, 2015.
Office Action for U.S. Appl. No. 15/087,415, dated May 23, 2016.
Office Action for U.S. Appl. No. 15/290,593 dated Jan. 2, 2018.
Office Action for U.S. Appl. No. 15/290,593, dated Aug. 1, 2018.
Office Action for U.S. Appl. No. 15/415,464 ,dated Mar. 15, 2017.
Office Action for U.S. Appl. No. 15/940,150, dated May 16, 2018.
Office Action for U.S. Appl. No. 15/955,455, dated Jun. 26, 2018.
Ogata and Sawaki, et al., "Kinetics of the Acid-Catalysed Formation of Aliphatic Peracids from Hydrogen Peroxide and Aliphatic Acids in Dioxin" Tetrahedron, 21:3381-3386, (1965).
Olaplex "The Olaplex Difference" https://olaplex.com/pages/how-it-works, retrieved from the internet Dec. 12, 2017.
PGR 2017-00012—Redacted version of Paper 102, Final Written Decision, Jun. 27, 2018 (Paper 105).
PGR 2017-00012 Liqwd, Inc.'s Patent Owner Response under 37 C.F.R. §42.220, filed on Oct. 20, 2017 (Redacted).
PGR 2017-00012 Patent Owner's First Amended Rule 30(b)(6) Deposition Notice, May 2, 2017.
PGR 2017-00012 Patent Owner's Supplemental Response, Novelty, May 24, 2018.
PGR 2017-00012 Petitioner's Reply to Patent Owner's Supplemental Response May 31, 2018.
PGR 2017-00012 Redacted Petitioners reply to patent owner's response, pp. 1-32 Jan. 26, 2018.
PGR 2018-00023—Wickett, Randall Declaration.
PGR 2018-00023 Paper 9 Institution Denied, Aug. 10, 2018.
PGR 2018-00023 Patent owner's preliminary response, pp. 1-76, May 21, 2018.
PGR 2018-00023 Redacted Petition for Post-Grant review of U.S. Pat. No. 9,668,954.
PGR 2018-00024—Wickett, Randall Declaration.
PGR 2018-00024 Paper 12 Institution Denied, Aug. 10, 2018.
PGR 2018-00024 Patent owner's preliminary response, pp. 1-76, May 21, 2018.
PGR 2018-00024 Redacted Petition for Post-Grant review of U.S. Pat. No. 9,668,954.
PGR 2018-00025—Wickett, Randall Declaration.
PGR 2018-00025 Paper 12 Institution Decision, Aug. 10, 2018.

(56) References Cited

OTHER PUBLICATIONS

PGR 2018-00025 Patent owner's preliminary response, pp. 1-51, May 21, 2018.
PGR 2018-00025 Petition for Post-Grant review of U.S. Pat. No. 9,668,954 (Redacted).
Po and Senozan article re: Henderson-Hasselbalch Equation, 2001 (Exhibit 2052).
Quantitative Chemical Analysis, pp. 1027-1 thru 1027-5, Daniel Harris Editor, 3rd Ed., (1991).
Redken Flash Lift Lightening Powder Label and Instructions.
Redken Up to 7 Bleach Powder Label and Instructions.
Robbins and Crawford, et al., "Cuticle Damage and the Tensile Properties of Human Hair", J. Soc. Cosmet. Chem. , 42, 59-67 (1991).
Robbins Chapter 5 Bleaching and Oxidation of Human Hair, 2012.
Robbins, et al., "Chemical Composition of Different Hair Types" Chemical and Physical Behavior of Human Hair ,Chapter 2:104-76, Springer-Verlag, Berlin Heidelberg (2012).
Robbins, et al., "Dyeing Human Hair", Chemical and Physical Behavior of Human Hair, Chapter 7, Springer-Verlag, Berlin Heidelberg (2012).
Robbins, et al., "The Physical Properties of Hair Fibers", Chemical and Physical Behavior of Human Hair, Chapter 9, Springer-Verlag, Berlin Heidelberg (2012).
Second Written Opinion for corresponding Singapore Application No. 11201609005Q dated Nov. 29, 2017.
Sigma-Aldrich website "BM(PEG)3 (1,11-bismaleimido-triethyleneglycol)".
Statement—Amended Reply Statement of Case on Validity (KR970, WO768 and Catzy), dated Nov. 28, 2017.
Statement—Reply Statement of Case on Validity (Olaplex), dated Nov. 28, 2017.
Statement of Case on the Term "Simple Salt", dated Jan. 10, 2018.
Statement of Case on Validity (KR970, WO768 and Catzy), dated Nov. 6, 2017.
Swift, Chapter 10, "Mechanical Properties of Hair" in Fundamentals of Human Hair Science, (1997).
Swift, Chapter 11, "Cosmetic Treatments of Hair" in Fundamentals of Human Hair Science, (1997).
Table 2 from Furia, T.E., Sequestrants in Food (Chp. 6) in CRC Handbook of Food Additives (1972).
Table 3.4, pKa values of some amino acids, From: Appendix: Acid-Base Concepts Biochemistry 5th edition. Berg JM, Tymoczko JL, Stryer L.New York: W H Freeman; (2002).
Thermo Scientific, "Instructions BM(PEG)2 and BM(PEG)3".
Third Party Observation filed in AU 2017251818, mailed Jan. 17, 2018.
Third Party Observation filed in ID Application No. P00201608726, mailed Mar. 6, 2018.
Third Party Observation filed in IN 2016177038524 on Feb. 6, 2019.
Third Party Observation filed in JP Application No. 2016-572832,mailed May 25, 2018, with English Summary).
Third Party Observation filed in KR 101787310 on Jan. 20, 2019.
Third Party Observation filed in MX Application No. MX/a/2016/014917 mailed Nov. 6, 2017.
Third Party Observation filed in NZ Application No. 725652, mailed May 16, 2018—Part 2 of 2.
Third Party Observation filed in NZ Application No. 725652, mailed May 16, 2018—Part 1 of 2.
Third Party Observation filed in U.S. Appl. No. 15/087,415, Aug. 29, 2016.
Third Party Observation filed in U.S. Appl. No. 15/087,415, Sep. 14, 2016.
Third Party Observation filed in U.S. Appl. No. 15/087,415, Sep. 23, 2016.
Third Party Observation filed in U.S. Appl. No. 15/087,415, Aug. 25, 2016.
Third Party Observation for (Israel) 248989, mailed Oct. 3, 2018.
Third Party Observation for EA 201692315, filed Nov. 1, 2017, English Translation.
Third Party Observation for EC IEPI 2016-94261, filed Mar. 29, 2017, with English Sumamry.
Third Party Observation for GB 1605346.4 , dated Oct. 24, 2018.
Third Party Observation for GB 1605346.4, filed Nov. 30, 2018.
Third Party Observation for GB 1813313.2, dated Jan. 8, 2019.
Third Party Observation, EP 15725209.9, mailed Aug. 22, 2018.
Third Party Protest filed in CA 2,947,303, mailed May 8, 2018.
Third Party Protest filed in CA 2,947,303, mailed Dec. 7, 2017.
Third Party Protest for CA 2947303, mailed Feb. 8, 2017.
Third Party Submission for CA 2,947,303, dated Sep. 14, 2018.
UK High Court Judgement—Jun. 11, 2018—in Relationship to GB 2525793.
White and Emmons, et al., "The Chemistry of Permaleic Acid", Tetrahedron, 17:31-34, (1962).
Wicket and Jachowicz, "Measuring Hair", Handbook of Cosmetic Science and Techonologypp. 694-724 Andre Barrel #rd. Ed, (2009).
Wickett, Randall R, PhD CV.
Written Opinion for PCT/US2015/031166 dated Jul. 19, 2016.
Zhao, et al., "Preparation of peracetic acid from hydrogen peroxide Part I: Kinetics for peracetic acid synthesis and hydrolysis" Journal of Molecular Catalysis A: Chemical, 271:246-252 (2007).
Zviak & Millequant Chapter 7, "Hair Bleaching" in The Science of Hair Care, (2005) (Exhibit DH 3).
Zviak & Millequant Chapter 9 "Oxidation Colouring", The Science of Hair Care, Informa Healthcare USA, Inc (2008).
Amazon.com Joico Vero K Pak Veroxide Developer Cream 32 ounce Beauty.
Bolduc, C. et al., "Hair Care Products: Waving, Straightening, Conditioning, and Coloring" Clinics in Dermatology 19:431-436 (2001).
Declaration of Thomas Dispenza, signed Oct. 17, 2017, filed in PGR 2017-00012.
Doering, et al., "Super mild oxidation coloring: preventing hair damage at the molecular lever", IFSCC Magazine, 10(4):323-9 (2007).
Office Action for CA 2,947,303 dated Sep. 8, 2017.
Redacted Declaration of Dean Christal, signed Oct. 18, 2017, filed in PGR 2017-00012.
Redacted Declaration of Edward T. Borish, Ph.D., signed Oct. 20, 2017, filed in PGR 2017-00012.
Redacted Declaration of Eric D. Pressly, Ph.D., signed Oct. 19, 2017, filed in PGR 2017-00012.
Redacted Liqwd, Inc.'s Patent Owner Response under 37 C.F.R. §42.220, filed in PGR 2017-00012 on Oct. 20, 2017.
Robbins, Chapter 4 "Bleaching Human Hair", in Chemical and Physical Behavior of Human Hair, 2002.
Robbins, Chapter 5 "Bleaching and Oxidation of Human Hair" in Chemical and Physical Behavior of Human Hair, 2012.
Robbins, Chapter 6 "Interactions of Shampoo and Conditioner Ingredients with Hair" in Chemical and Physical Behavior of Human Hair, 2012.
Second Examination Report for AU 2015258904 dated Oct. 26, 2017.
Second Examination Report for NZ 725652 dated Oct. 13, 2017.
Third Party Observation for AU 2015258904 mailed Oct. 5, 2017.
Third Party Observation for EP 15725209.9 mailed Oct. 27, 2017.
Third Party Observation for JP 2016-572832 mailed Sep. 29, 2017.
English Summary of Office Action IL 248989 (with Third Party Submission) dated Sep. 6, 2017.
Clarence R. Robbins,Mouhatu no kagaku [Science of Hair], 4th edition,FragranceJournal Ltd.,Jul. 10, 2006,p. 221-225 with English counterpart, p. 194-198.
Decision, denying Institution of Post-Grant Review, by Patent Trial and Appeal Board in PGR 2017-00011 (Jul. 19, 2017).
Decision, partial Institution of Post-Grant Review, by Patent Trial and Appeal Board in PGR 2017-00012 (Jul. 19, 2017).
English Translation of KR2006-0059564.
Examination Report for Saudi Arabia Patent Application No. 516370509, dated May 25, 2017(with English summary).

(56) References Cited

OTHER PUBLICATIONS

Keshouhin kagaku guide [Cosmetic Science Guide] 2nd edition,FragranceJournal Ltd.,May 16, 2011,p. 256-257 with English description.
Memorandum Order in *Liqwd, Inc. et al.* v. *L'Oréal USA, Inc. et al.*, Case No. 1:17-cv-00014 (D. Del), denying Motion for Preliminary Injunction by Judge Sue L. Robinson (Jul. 6, 2017).
New Zealand Examination Report for corresponding New Zealand Application No. 725652 dated Apr. 3, 2017.
Office Action for Canada Patent Application No. 2,947,303, dated May 12, 2017.
Office Action for Chinese Patent Application No. 201480042200.1, dated May 2, 2017(with English summary).
Office Action for Colombian Patent Application No. 16-030.965, dated Jul. 28, 2017 (with English summary).
Office Action for Georgia Patent Application No. AP 2014 01404, dated May 4, 2017 (with English translation).
Office Action for Israel Patent Application No. 248989, dated Jun. 5, 2017. (with English summary).
Office Action for Japanese Patent Application No. 2016-572832, dated Jun. 2, 2017 (with English summary).
Office Action for Korean Patent Application No. 10-2016-7034158, dated Apr. 10, 2017(with English summary).
Office Action for Panama Patent Application No. 91008-01, dated Jan. 31, 2017(with English summary).
Office Action for Panama Patent Application No. 91418-01, dated Jun. 8, 2017. (with English summary).
Office Action for Ukraine Patent Application No. a201601137, dated Jun. 22, 2017 (with English translation).
Office Action for United Kingdom Patent Application No. 1618547. 2, dated Nov. 30, 2016.
Office Action for United Kingdom Patent Application No. GB1605344. 9, dated Apr. 29, 2016.
Redacted Version of Declaration of Robert .W. J. Hefferd, PhD_PART_1of3; with Appendices (1-3) and Exhibits (A-O), filed in *Liqwd, Inc. et al.* v. *L'Oréal USA, Inc. et al.*, U.S. District Court for the District of Delaware, Civil Action No. 1:17-cv-00014 on Apr. 17, 2017.
Redacted Version of Declaration of Robert .W. J. Hefferd, PhD_PART_2of3; with Appendices (1-3) and Exhibits (A-O), filed in *Liqwd, Inc. et al.* v. *L'Oréal USA, Inc. et al.*, U.S. District Court for the District of Delaware, Civil Action No. 1:17-cv-00014 on Apr. 17, 2017.
Redacted Version of Declaration of Robert .W. J. Hefferd, PhD_PART_3of3;with Appendices (1-3) and Exhibits (A-O), filed in *Liqwd, Inc. et al.* v. *L'Oréal USA, Inc. et al.*, U.S. District Court for the District of Delaware, Civil Action No. 1:17-cv-00014 on Apr. 17, 2017.
Redacted Version of Defendant's Brief in Opposition to Plaintiff's Motion for Preliminary Injunction, by L'Oreal USA Products, Inc., et al., filed in *Liqwd, Inc. et al.* v. *L'Oréal USA, Inc. et al.*, U.S. District Court for the District of Delaware, Civil Action No. 1:17-cv-00014 on Apr. 17, 2017.
Australian Examination Report AU 2015258904 dated Nov. 2, 2016.
Canadian Office Action 2,947,303 dated Dec. 28, 2016.
Protest Canadian Application 2,947,303 mailed Feb. 8, 2017.
Third Party Observation Australia AU 2015258904 mailed Dec. 19, 2016.
Third Party Observation New Zealand NZ 725652 mailed Dec. 19, 2016.
Berth and Reese, "Veranderung des haarkeratins durch kosmetische behandlung und naturliche umwelteinflusse", J Soc Cos Chem., 15:659-66 (1964).
Certified Engiish Translation of DE1220969.
Certified English Translation of KR2006-0059564.
Combined Search and Examination Report GB 1618423.6 dated Nov. 29, 2016.
Davies and Evans, "The isomerization of maleic acid in aqueous solutions", Transections of Faraday Society, Chapter 52:74-80 (1956).

Declaration of Arun Nandagiri dated Jan. 30, 2017, with curriculum vitae.
Declaration of Arun Nandagiri dated Jan. 31, 2017, with curriculum vitae.
Declaration of Edward T. Borish in Support of Olaplex\s Motion for a Preliminary Injunction , filed Jan. 18, 2017, with curriculum vitae.
Engel, et al., "Fumaric acid production by fermentation", App Microbiol Biotechnol, 78:379-89 (2008).
Examination Report GB1605346.4 dated Jan. 11, 2017.
Examination Report AU2015058904 dated Nov. 2, 2016.
Facebook page, https://www.facebook.com/behindthechair/photos/a.153398501906.116563.44389181906/10152417864161907/?type=3&theater ; May 13, 2014.
Facebook page, https://www.facebook.com/GuyTangHairArtist/photos/a.254923251198058.69129.214382105252173/762062380484140/?type=3&theater; Apr. 17, 2014a.
Facebook page, https://www.facebook.com/GuyTangHairArtist/photos/a.254923251198058.69129.214382105252173/762551773768534/?type=3&theater ; Apr. 17, 2014b.
Facebook page, https://www.facebook.com/GuyTangHairArtist/photos/a.254923251198058.69129.214382105252173/767530266604018/?type=3&theater ; Apr. 26, 2014.
Facebook page, https://www.facebook.com/GuyTangHairArtist/photos/a.254923251198058.69129.214382105252173/772484942775217/?type=3&theater; May 7, 2014.
Facebook page, https://www.facebook.com/olaplex/573114059463275; Apr. 7, 2014.
Facebook page, https://www.facebook.com/olaplex/photos/a.541423639298984.1073741828.347578558683494/574713415970006/?type=3&theater; Apr. 11, 2014.
Facebook page, https://www.facebook.com/traceycunninghamcolor/posts/10152466366701095; May 11, 2014.
Facebook page, https://www.facebook.com/traceycunninghamcolor/posts/10202245158143314; Mar. 9, 2014.
Grounds of Invalidity filed by L'Oreal (UK) Limited, et al., on Nov. 4, 2016.
Guy Tang on Instagram page, https://www.instagram.com/p/nPrnHn7rnnA6/; Apr. 26, 2014.
Hierarchical Structure, https://www.upload.wikimedia.org/wikipedoa/commons/thumb/5/55/Hierarchical_structure, retrieved from the internet Sep. 22, 2016.
International Search Report and Written Opinion for PCT/US2016/058432, dated Jan. 16, 2017.
Jachowicz, "Hair damage and attempts to its repair". J Soc Cosmet Chem., 38:263-86 (1987).
Japanese Office Action for JP 2016-515948 dated Jan. 25, 2017 (with English Translation).
John Corbett, Hair Colorants: Chemistry and Toxicology 1-54 (1998).
Olaplex on Instagram page, https://www.instagram.com/p/m/GhswioJQ2/?hl=en; Mar. 28, 2014.
Olaplex on Instagram page, https://www.instagram.com/p/mvxsbUoJSI/?hl=en; Apr. 13, 2014.
Olaplex on Instragram page, https://www.instagram.com/p/nBwLbtoJck/?hl=en; Apr. 20, 2014.
Olaplex, Material Safety Data Sheet for Olaplex Bond Multipler No. a Dec. 2014.
Partial International Search Report for PCT application, PCT/US2015/065032, dated May 9, 2016.
Petition for Post-Grant Review of U.S. Pat. No. 9,498,419, filed on behalf of L'Oreal USA, Inc. (dated Jan. 31, 2017) (PGR 2017-00012).
Petition for Post-Grant Review of U.S. Pat. No. 9,498,419, filed on behalf of L'Oreal USA, Inc. (dated Jan. 31, 2017) (PGR 2017-00011).
Plaintiff's Opening Brief in Support of Motion for Preliminary Injunction, redacted—public version, filed Jan. 18, 2017.
Pramanik, "10.3.7 DS-Salt Interaction", Characterization of Impurities and Degradants Using Mass Spectrometry, John Wiley & Sons, Hoboken, New Jersey, (2011).
Ramachandra, et al., "Acid-based characteristics of human hair: Absorption of HCl and HaOH, and the effects on physical properties." J Soc Comet Chem., 32:393-405 (1981).

(56) References Cited

OTHER PUBLICATIONS

Randebrock, "Neue Erkenntnisse Uber den morphologischen aufbau des menschlichen haares," J Soc Cos. Chem., 15:691-706 (1964).
Relaxing agents, Milday agents, Milday Standard Cosmetology, pp. 618-625, 13th edition, (2016).
Third Party Observation filed GB1605346.4 (Nov. 11, 2016).
Third Party Observatlon mailed EP14758005.4 (Dec. 21, 2016).
Third Party Observation mailed EP157250209.9 (Jan. 10, 2017).
Thomas Clausen et al., Hair Preparations, in Ullman's Encyclopedia of Industrial Chemistry (Jul. 15, 2006).
Tracey Cunningham on Instagram page; https://www.instagram.com/p/l1AF_Zig5e/; Mar. 22, 2014.
Tracey Cunningham on Instagram page, https://www.instagram.com/p/l_mat6ig-z/; Mar. 26, 2014.
Webster's Third International New Dictionary 40 (3rd ed) 2002.
Whewell, "The chemistry of hair", pp. 207-223 A lecture delivered before the Society Dec. 14, 1960.
Combined Search and Examination Report for GB 1523109.5 dated Feb. 4, 2016.
Combined Search and Examination Report dated Sep. 14, 2015 in connection with UK patent application, GB1513932.2.
Dombrink and Tanis "pH & hair shampoo," Chem Matters, p. 8 (1983).
Examination Report for GB 1513932.2 dated Sep. 26, 2016.
Expert Village, Hair color mixing and application techniques: Mixing bleach for highlights, https://www.youtube.com/watch?v=nOE_BaC57mw, 3 pages, retrieved from the internet May 17, 2016.
Halal "The Chemistry of Haircolor," Slide 36, http://chemistrysimplified.com/wp-content/uploads/2015/07/CEA-2015-Chemistry-of-Haircolor.pdf (2015).
Hall and Wolfram, "Application of the theory of hydrophobic bonds to hair treatments," J Soc Cosmet Chem., 28:231-41 (1977).
International Search Report and Written Opinion for PCT/US2014/049388 dated Oct. 29, 2014.
International Search Report and Written Opinion for PCT/US2016/029215 dated Jul. 8, 2016.
International Search Report and Written Opinion or PCT/US2015/031166, dated Jan. 22, 2016.
International Search Report and Written Opinion for PCT application, PCT/US2015/065032, dated May 9, 2016.
Japanese Office Action for JP 2016-515948 dated Jul. 29, 2016 (with English Translation).
Koval, "Reactions of Thiols," Russian J Organic Chemistry, 43(3):319-49 (2007).
Lab muffin "How Does Olaplex Hair Treatment Work?" http://www.labmuffin.com/2015/04/how-does-hair-treatment-work, 8 pages retrieved from the internet Jun. 24, 2016.
Majonis, et al., "Dual-purpose polymer labels for fluorescent and mass cytometric affinity bioassays," Biomacromolecules, 14(5):1503-13 (2013).
Mintel Database, Record ID 743114, Catzy Hair Colourant, 4 pages, Published Jul. 2007.
Minitel Leave-in Hair and Scalp Nutrient, XP002743522, Database accession No. 10141004, Jun. 1, 2003.
Mintel Permanent Hair Colour, XP002743523 Database Accession No. 2061070, May 1, 2013.
Notification of Grant for GB 1313532.2 dated Oct. 4, 2016.
Official communication GB 1513932.2 (dated Apr. 13, 2016).
Olaplex on Instagram, http://www.instagram.com/p/zacpQuIJfn/, Instagram post Feb. 22, 2015.
Partial International Search Report for PCT/US2015/031166, dated Sep. 14, 2015.
Refinery, "Fire Your Colorist if They Are Not Using This" http://www.refinery20.com/olaplex-hair-color, 6 pages, retrieved from the internet Jun. 24, 2016.
Shansky, "Toning of Human Hair with Fiber Reactive Dyestuffs," Cosmetics and Tolietries, 91(11):46-48 (1976).
Shansky,"The Reaction Mechanism of Fiber Reactive Dye stiffs with Hair Keratin," American Perfumer and Cosmetics (1966).

Slavin, et al. "Biological surface modification by thiol-ene\ addition of polymers synthesized by catalytic chain transfer polymerization (CCTP)," Polymer Chem., 3:1461-6 (2012).
The Power of One http://www.nxtbook.com/nctbooks/creativage/Launchpad_201405/index.php?srartid, 401 page, retrieved from the internet Jun. 24, 2016.
Thermo Fisher Scientific ,"Bismaleimide Cross linkers (BMOE, BMBandBMH)," product instructions, pp. 1-3(2012).
Third Party Observation filed in European Application No. 14758005.4 (May 13, 2016).
Third Party Observation filed in European Application No. 14758005.4 (May 18, 2016).
Third Party Observation filed in GB 1513932.2 (Jan. 2016).
Third Party Observation filed in GB 1513932.2 (Oct. 3, 2016).
Third Party Observation filed in GB 1513932.2 (Sep. 22, 2016).
Third Party Observation filed in GB 1513932.2 (Aug. 23, 2016).
Third Party Observation for GB1513932.2 (Jun. 24, 2016).
Third Party Observation Submitted in GB 1513932.2 (Apr. 20, 2016).
WPI Accession No. 1995-355152, English abstract of JPH07242520, Sep. 9, 1995, retrieved Feb. 2, 2016.
Written Opinion for PCT/US2016/031166 dated Jul. 19, 2016.
Yan, et al., "Cellularassociationandcargoreleaseofredox-responsive polymercapsulesmediatedbyexofacialthiols," Adv. Mater. ,2011, 23, 3916-3921.
Zviak "The Science of Hair Care," Marcel Dekker, Inc., pp. 263-279(1986).
Amazon.com Joico Vero K Pak Veroxide Developer Cream 32 ounce Beauty, filed Jan. 29, 2019.
Aparecida Da Franca, et al., "Types of Hair Dye and Their Mechanisms of Action", Cosmetics 2,110-126, 2015.
Borish, Edward T. CV filed Nov. 16, 2018.
Brown and Pohl, Permanent Hair Dyes, Society of Cosmetic Chemists,pp. 1-41, 1996.
E-mail correspondence regarding documentary evidence as provided by the third party (Ex 36), filed May 16, 2018.
English Translation of Packaging in Mintel Database, Record ID 743114, Catzy Hair Colourant, Published Jul. 2007. Translation Filed Feb. 2, 2018.
Ex 1048, PGR 2018-00025, Public version of Ex 1036, Laboratory Notebook, filed Oct. 10, 2018.
Ex 1063; Signori, International Journal of Cosmetic Science; 1997.
Ex 1065; Practical Modern Hair, Science, Chapter 4; 2012.
Ex 2010, pGR 2018-00023, Joico Bleach Powder label with instructions and ingredients, filed May 21, 2018.
Ex 2011, PGR 2018-00023, Clairol Professional Basic White Powder Lightener label with instructions and ingredients filed May 21, 2018.
Ex 2024, PGR 2018-00023, Matrix Light Master Bleach Powder label and instructions, filed May 21, 2018.
Ex 2025, PGR 2018-00023, Redken Flash Lift Lightening Power label and instructions, filed May 21, 2018.
Ex 2026, PGR 2018-00023, Redken Up to 7 Bleach Powder, label and instructions, filed May 21, 2018.
Ex 2027, PGR 2018-00023, L'Oreal Quick Blue Bleach Powder label and instructions, filed May 21, 2018.
Ex 2045, PGR 2018-00025, Matrix Bond Ultim8 Techniques Guide, filed Nov. 16, 2018.
Ex 2047, PGR 2018-00025, Matrix Bond Ultim8 bottle instructions, filed Nov. 16, 2018.
Ex 2048, pGR 2018-00025, Matrix Bond Ultim8 package instructions, filed Nov. 16, 2018.
Ex 2049, PGR 2018-00025, Lab report from Analyze Inc., filed Nov. 16, 2018.
Ex 2050, PGR 2018-00025, Redken pH Bonder bottle instructions, filed Nov. 16, 2018.
Ex 2051, PGR 2018-00025, Redken pH Bonder package instructions, filed Nov. 16, 2018.
Ex 2052, PGR 2018-00025, L'Oreal Professional Smartbond bottle instructions, filed Nov. 16, 2018.
Ex 2053, PGR 2018-00025, L'Oreal Professional Smartbond package instructions, filed Nov. 16, 2018.

(56) References Cited

OTHER PUBLICATIONS

Ex 2075, PGR 2018-00025, Redacted LIQWD Inc. Patent Owner Response under 37 CFR 42.220, dated Nov. 16, 2018.
HiMedia Labs, http://www.himedialabs.com/TD/AT068.pdf, downloaded on Mar. 6, 2018, pp. 1-2, 2011.
INCI listing ingredient BIS Aminopropyl Diglycol Dimaleate Cosmetics Cosing EC Regulation v2, Mar. 29, 2018.
Institution of Cancellation Proceeding for KR (Republic of Korea) 10-2016-7034158, dated May 17, 2018, with English Translation.
Joico VeroLight Dust-Free Lightening Powder Sleek Shop accessed Mar. 28, 2018.
Kirschenbaum, et al., "Oxygen radicals from photoirradiated human hair: An ESR and fluorescence study", J Cosmetic Sci, 51, 169-182, 2000.
Kline, htt://homepage.smc.edu/kline_peggy/Organic/Amino_Acid_pKa.pdf, obtained online on Mar. 6, 2019, p. 1, 2006.
KR 10-1787310 Decision on Cancellation Mar. 5, 2019 with Eng Translation.
L'Oreal Invalidity Opinion Ex A01, filed Jul. 26, 2018.
L'Oreal Invalidity Opinion Ex A02, filed Jul. 26, 2018.
L'Oreal Invalidity Opinion Ex A03, filed Jul. 26, 2018.
L'Oreal Invalidity Opinion Ex A04, filed Jul. 26, 2018.
L'Oreal Invalidity Opinion Ex A05, filed Jul. 26, 2018.
L'Oreal Invalidity Opinion Ex A06, filed Jul. 26, 2018.
L'Oreal Invalidity Opinion Ex A07, filed Jul. 26, 2018.
L'Oreal Invalidity Opinion Ex A08, filed Jul. 26, 2018.
L'Oreal Invalidity Opinion Ex A09, filed Jul. 26, 2018.
L'Oreal Invalidity Opinion Ex A10, filed Jul. 26, 2018.
L'Oreal Invalidity Opinion Ex A11, filed Jul. 26, 2018.
L'Oreal Invalidity Opinion Ex A12, filed Jul. 26, 2018.
L'Oreal Invalidity Opinion Ex A13, filed Jul. 26, 2018.
L'Oreal Invalidity Opinion Ex A14, filed Jul. 26, 2018.
L'Oreal Invalidity Opinion Ex A15, filed Jul. 26, 2018.
L'Oreal Invalidity Opinion Ex A16, filed Jul. 26, 2018.
L'Oreal Invalidity Opinion Ex A17, filed Jul. 26, 2018.
L'Oreal Invalidity Opinion Ex A18, filed Jul. 26, 2018.
L'Oreal Invalidity Opinion Ex A19, filed Jul. 26, 2018.
L'Oreal Invalidity Opinion Ex A20, filed Jul. 26, 2018.
L'Oreal Invalidity Opinion Ex A21, filed Jul. 26, 2018.
L'Oreal Invalidity Opinion Ex A22, filed Jul. 26, 2018.
L'Oreal Invalidity Opinion Ex A23, filed Jul. 26, 2018.
L'Oreal Invalidity Opinion Ex A24, filed Jul. 26, 2018.
L'Oreal Invalidity Opinion Ex A25, filed Jul. 26, 2018.
L'Oreal Invalidity Opinion Ex A26, filed Jul. 26, 2018.
L'Oreal Invalidity Opinion Ex A27, filed Jul. 26, 2018.
L'Oreal Invalidity Opinion Ex A28, filed Jul. 26, 2018.
L'Oreal Invalidity Opinion Ex A29, filed Jul. 26, 2018.
L'Oreal Invalidity Opinion Ex A30, filed Jul. 26, 2018.
L'Oreal Invalidity Opinion Ex A31, filed Jul. 26, 2018.
L'Oreal Invalidity Opinion Ex A32, filed Jul. 26, 2018.
L'Oreal Invalidity Opinion Ex A33, filed Jul. 26, 2018.
L'Oreal Invalidity Opinion Ex A34, filed Jul. 26, 2018.
L'Oreal Invalidity Opinion Ex A35, filed Jul. 26, 2018.
L'Oreal Invalidity Opinion Ex A36, filed Jul. 26, 2018.
L'Oreal Invalidity Opinion Ex A37, filed Jul. 26, 2018.
L'Oreal Invalidity Opinion Ex A38, filed Jul. 26, 2018.
L'Oreal Invalidity Opinion Ex A39, filed Jul. 26, 2018.
L'Oreal Invalidity Opinion Ex A40, filed Jul. 26, 2018.
L'Oreal Invalidity Opinion Ex A41, filed Jul. 26, 2018.
L'Oreal Invalidity Opinion Ex A42, filed Jul. 26, 2018.
L'Oreal Invalidity Opinion Ex A43, filed Jul. 26, 2018.
L'Oreal Invalidity Opinion Ex A44, filed Jul. 26, 2018.
L'Oreal Invalidity Opinion Ex A45, filed Jul. 26, 2018.
L'Oreal Invalidity Opinion Ex A46, filed Jul. 26, 2018.
L'Oreal Invalidity Opinion Ex A47, filed Jul. 26, 2018.
Mintel Database Record ID 1999129, L'Oreal Preference Les Blondissimes Hair Colourant, 2013.
Murota, et al. J Investig Allergol Clin Immunol, 18(4):245-252, (2008).
Office Action for AU (Australia) 2017251818, dated May 31, 2019.
Office Action for CA (Canada) 2,947,303, dated Mar. 19, 2019.
Office Action for CN (China) 201480042200.1 with English summary, dated Apr. 22, 2019.
Office Action for CN (China) 201580026038.9 with English summary, dated Apr. 11, 2019.
Office Action for EA (Eurasia) 2016-92315 dated Jan. 30, 2019 with English Summary.
Office Action for EA (Eurasia) 201692315 mailed with English translation, dated Sep. 28, 2017.
Office Action for EP (Europe) 15725209.9 dated May 16, 2019.
Office Action for EP (Europe) 16798857.5 dated Feb. 19, 2019.
Office Action for ID P00201600646, dated Jan. 21, 2019 with English Translation.
Office Action for JP (Japan) 2016-572832 with English summary, dated Dec. 11, 2018.
Office Action for JP (Japan) 2017-152453 dated May 14, 2019, English summary.
Office Action for JP (Japan) 2017-152453 with English summary, dated Oct. 30, 2018.
Office Action for U.S. Appl. No. 15/626,453 dated May 14, 2019.
Office Action for U.S. Appl. No. 15/854,504, dated Mar. 7, 2019.
PGR 2018-00025; Ex 1062; Wickett Reply Declaration, Redacted, dated Feb. 15, 2019.
Robbins, Chapter 10, Chemical and Physical Behavior of Human Hair, 5th Edition, 2012.
Sigma-Aldrich website BM PEG 3 1 11 Bismaleimido Triethyleneglycol (2018).
Thermo Scientific, "Instructions BM (PEG) 2 and BM (PEG) 3" (2012).
Third Party Observation for JP (Japan) 2016-572832 with English Translation dated Apr. 19, 2019.
Third Party Observation IL (Israel) 248989 dated Jan. 10, 2018.
Third Party Observation AU (Australia) 2017251818 filed Jun. 4, 2019.
Third Party Observation BR (Brazil) 1120160263782 Jan. 9, 2018 w/Eng Summary.
Third Party Observation BR (Brazil) 1120160263782 Oct. 23, 2018 w/Eng Summary.
Third Party Observation CA (Canada) 2947303 filed Feb. 19, 2019.
Third Party Observation EP (Europe) 15725209.9 filed Feb. 22, 2019.
Third Party Observation EP (Europe) 15725209.9 filed Feb. 22, 2019 with Eng Translation.
Third Party Observation for EP (Europe) 15725209.9 filed May 8, 2019.
Third Party Observation GB 1813313.2 filed Apr. 2, 2019.
Third Party Observation GB 1813313.2 filed Mar. 8, 2019.
Third Party Observation IN (india) 2016177038524 on Feb. 6, 2019.
Third Party Observation JP 2016572832 filed Mar. 5, 2019 with Eng Summary.
Third Party Observation KR (Korea) 101787310 on Jan. 29, 2019.
Third Party Observation KR 101787310 filed Jan. 29, 2019 with Eng Translation.
Third Party Obsevation CA (Canada) 2947303 filed Jun. 12, 2019.
Examination Report PH (Philippines) 1-2016-500132, dated Oct. 29, 2019.
Fragrance Journal, 49-56 (Jan. 1997).
Imai, et al., "The Dyeing Mechanism of Oxidative Hair Color in White and Black Human Hair", J. Soc. Cosmet. Chem. Jpn., 44 (3):208-215 (2010) with English Abstract.
Joko, et al., "A Tentative Mechanism of Oxidative Dyeing for Keratin Fibers", J. Soc. Cosmet. Chem. Jpn., 42 (3):185-200 (2008) with English Abstract.
*L'Oreal* vs. *Olaplex* Judgement UK 2019 EWCA CIV 1943, dated Nov. 18, 2019.
Office Action BR (Brazil) 112016026378-2 dated Oct. 15, 2019, with English Summary.
Office Action Japanese Appeal No. 2018-15999; JP (Japan) 2016-572832 dated Nov. 19, 2019 with English Translation.
Third Party Observation EA (Eurasia) 201692315, dated Sep. 13, 2019, with English Translation.
Third Party Observation EP (Europe) 15725209.9 filed Nov. 15, 2019.

(56) References Cited

OTHER PUBLICATIONS

Third Party Observation EP (Europe) 15725209.9 dated Nov. 29, 2019.
Asquith, et al., Chemistry of Natural Protein Fibers (1977).
B(l)ack to blonde article, behindthechair.com accessed Jan. 1, 2019.
Brown, Excerpts from the 5th Edition of Organic Chemistry, (2011).
Canari, "Effect of pH on Dicarboxylic Acids Extraction by Amine-Based Extractants", Ind. Eng. Chem. Res., 42:1293-1300 (2003).
Catzy Blonde Statement of the use of Maleic Acid, dated Dec. 1, 2017.
Central Role Presentation, dated Jan. 26, 2015.
Chan, "Nucleophile-Initiated Thiol-Michael Reactions: Effect of Organocatalyst, Thiol, and Ene", Macromolecule, 13:6381-6388 (2010).
Citraconic Acid, C5H604—PubChem, accessed Dec. 21, 2018.
Combined Search report and Examination Report in connection with UK patent application, GB1513932.2 dated Sep. 24, 2015.
Davis, et al., Excerpts from Modern Chemistry, pp. 214, 215, and 454 (1999).
Defendant-Intervenor brief in Appeal No. 2019Heo3618, KR (Korea) 1787310, dated Oct. 23, 2019.
Dmuchovsky, et al., "The Mechanism of the Base-Catalyzed Addition of Thiols to Maleic Anhydride", Free-Radical Addition of Thiols to Maleic Anhydride, 86:2875-2877 (1964).
English Translation of Defendant-Intervenor brief in Appeal No. 2019Heo3618, KR (Korea) 1787310, dated Oct. 23, 2019.
English Translation of KIPO Response Correction in Appeal No. 2019Heo3618, KR (Korea) 1787310, dated Oct. 22, 2019.
English Translation of KIPO Response in Appeal No. 2019Heo3618, KR (Korea) 1787310 dated Oct. 15, 2019.
Evans, et al., "A statistical analysis of hair breakage. II. Repeated grooming experiments", J. Cosmet. Sci., 61:440-455 (2010).
Fed Cir. decision in Appeal No. 2018-2152, Oct. 17, 2019.
Fibreplex No. 1 Bond Booster, Icare, accessed Oct. 11, 2017.
Fibreplex No. 1 Label, 6 pages, accessed Feb. 28, 2018.
Fibreplex Safety Date Sheet, 5 pages, issued Mar. 16, 2016.
Fueghelman, et al., "Morphology and Properties of Hair", Hair and Hair Care: Cosmetic Science and Technology Series, 17(1): 1-15 (1997).
Gamez-Garcia, et al., "Patterns of Light Interference", Journal of Cosmetic Science, 58(4): 269-282 (2007).
Gamez-Garcia, et al., "Understanding Properties of Hair Cuticle", Journal of Cosmetic Science, 423-424 (2006).
Gobbo, et al., "Improved Methodology for the Preparation of Water-Soluble, Malemide-Functionalized Small Gold Nanoparticles", Langmuir, ACS Publications, 28:12357-12363 (2012).
Haake, et al., "Hair breakage-How to measure and counteract", J. Cosmet. Sci., 60:143-151 (2009).
Halal, Hair Structure and Chemistry Simplified, 322 pages (2009).
Hoshowski, "Conditioning of Hair", Hair and Hair Care, 17(4):65-104 (1997).
Hoyle, et al., "Thiol-click chemistry: a multifaceted toolbox for small molecule and polymer synthesis", Chemical Society Reviews, 39:1355-1387 (2010).
Isaacman, "Just Click It: New Chemical Reactions for Cosmetic Applications", Cosmetics & Toiletries, https://www.cosmeticsandtoiletries.com/research/techtransfer/premium-Just-Click-It-New-Chemical-Reactions-for-Cosmetic-Applications-209714931.html, accessed Apr. 5, 2018.
Jankowksa, et al., "The Relations Between Ionic and Non-Ionic Diffusion of Sulfonamides Across the Rabbit Cornea", Investigative Ophthalmology & Visual Science, 27(1):29-37 (1986).
Kade, et al., "The Power of Thiol-ene Chemistry", J. Polymer Science Part A: Polym. Chem., 48:743-750 (2010).
Kang, "Hair Dyeing and Hair Damage According to the Number of Dyeing", Master's Thesis, Kwangju Women's University, 11-13 (2006) with English Translation.
KIPO Response Correction in Appeal No. 2019Heo3618, KR (Korea) 1787310 dated Oct. 22, 2019.
KIPO Response in Appeal No. 2019Heo3618, KR (Korea) 1787310 dated Oct. 15, 2019.
Kolb, et al., "Click Chemistry: Diverse Chemical Function from a Few Good Reactions", Agnew. Chem. Int. Ed., 40:2004-2021 (2001).
Lewis excerpt from Hawley's Condensed Chemical Dictionary, 5 pages (1997).
Mayo, et al., "Effect of Spacer Chemistry on the Formation and Properties of Linear Reversible Polymers", Journal of Polymer Chemistry, Part A: Polymer Chemistry, 51:5056-5066 (2013).
Mhaskar, et al., "Hair breakage index: An alternative tool for damage assessment of human hair", J. Cosmet. Sci., 62:203-207 (2011).
Morgan, et al., "Interaction of Maleic Acid with Thiol Compounds", Biochemical Laboratory, Cambridge, 733-742 (1983).
MSDS Olaplex No. 1 Bond Multiplier, dated Jun. 2014.
MSDS Olaplex No. 2 Bond Perfector, updated Jul. 2014.
Nair, et al., "The Thiol-Michael Addition Click Reaction: A Powerful and Widely Used Tool in Materials Chemistry", Chemistry of Materials, 26:724-744 (2014).
Naver Encyclopedia, Trichology Dictionary: Developer, with English Translation (2003).
New Olaplex Usage Instructions label (Jun. 2014).
Office Action ARIPO AP/P/2015/008934, dated May 27, 2019.
Office Action BR (Brazil) 1120160022556, dated Aug. 6, 2019, with English Summary.
Office Action BR (Brazil) 112016026378-2, dated Aug. 14, 2019, with English Summary.
Office Action CA (Canada) 2947303, dated Jul. 12, 2019.
Office Action CN (China) 201580026039, dated Jul. 16, 2019 with English Summary.
Office Action CU (Cuba) 2016-0017 dated Jul. 3, 2018 (with English Translation).
Office Action EA (Eurasia) 201592291, dated Jul. 9, 2019, with English Translation.
Office Action EA (Eurasia) 201692315, with English Translation, dated Oct. 23, 2019.
Office Action EP (Europe) 17163334, dated Jun. 18, 2019.
Office Action IN (India) 201647007019, dated Aug. 2, 2019 with English Translation.
Office Action MX (Mexico) MX/a/2016/014917, dated Apr. 12, 2019 with English Summary.
Office Action MY (Malaysia) PI 2016700195 dated Sep. 30, 2019.
Office Action SV (El Salvador) Application No. 2016-0019660 dated Mar. 18, 2019 with English Summary.
Office Action U.S. Appl. No. 15/854,504 dated Aug. 8, 2019.
Olaplex Bond Mulitplier No. 1 Mix with Highlights, balayage, or high lift color label (Jun. 2014).
Olaplex, Apparent description of booth presentation during Bronner Bros. show in Atlanta http://www.instagram.com/p/zacpQuIJfn/, Instagram post Feb. 22, 2015.
Olaplex.com, "Never break a client's hair", visited Jun. 28, 2014.
Paterson, et al., "On the synthesis of N-maleoyl amino acids in aqueous media: cautionary tales for the unwary traveller", ARKAT USA, Inc., 11-16 (2010).
Pomogailo, et al., "Monomeric and Polymeric Carboxylic Acids", Springer Series in Materials Science, 138(2):7-25 (2010).
Public Version of Final Written Decision, dated Jul. 30, 2019.
Robbins, et al., "Polymerization into Human Hair", J. Soc. Cosmet. Chem., 25:407-421 (1974).
Robinson, "A study of damaged hair", J. Soc. Cosmet. Chem., 27:155-161 (1976).
Ruetsch, et al., "Photodegradation of human air: An SEM study", J. Cosmet. Sci., 51:103-125 (2000).
Sandhu, et al., "A simple and sensitive method using protein loss measurements to evaluate damage to human hair during combing", J. Soc. Cosmet. Chem., 46:39-52 (1995).
Success Stories presentation, Oct. 6, 2016.
Swift, Fundamentals of Human Hair Science, (1997).
Tate, et al., "Quantification and prevention of hair damage", J. Soc. Cosmet. Chem., 44:347-371 (1993).
Third Party Observation AU (Australia) 2017251818, dated Jun. 17, 2019.

(56) References Cited

OTHER PUBLICATIONS

Third Party Observation AU (Australia) 2017251818, dated Oct. 2, 2019.
Third Party Observation CA (Canada) 2947303, dated Oct. 25, 2019.
Third Party Observation CA (Canada) 2947303, filed Jun. 12, 2019.
Third Party Observation EA (Eurasia), dated Sep. 13, 2019.
Third Party Observation JP (Japan) 2016-572832 filed Sep. 2, 2019 with English summary.
Voet, et al., Fundamentals of Biochemistry Excerpt (2008).
Wenniger, et al., "Maleic Acid", CTFA Cosmetic Ingredient Handbook, 2:226 (1992).
Yang, et al., "In-Situ Polymerization of Maleic Acid and Itaconic Acid and Crosslinking of Cotton Fabric", Textile Res. J., 69(10):782-789 (1999).
Yang, et al., "Polymerization of Maleic Acid and Itaconic Acid Studied by FT-Raman Spectroscopy", J. Applied Polymer Science, 81:223-228 (2001).
Zumdahl, Chemistry Excerpt, 15:621-622 (1986).
Zviak, et al., "Hair Structure, Function, and Physicochemical Properties", The Science of Hair Care, Chapter 1, 1-48 (1986).
English Summary of Office Action for IL (Israel) 248989 dated Mar. 13, 2020.
English Translation of Japanese Office Action for JP 2017-555304 dated Mar. 18, 2020.
English Translation of Third Party Observation BR (Brazil) 1120160263782 Mar. 17, 2020.
Japan Cosmetic Industry Association ed., 1st Ed., Japan Cosmetic Industry Association, 139-142 with English Summary (2012).
Memorandum in Response to Official Action dated Oct. 7, 2018 in Israel application No. 248989 dated Jan. 24, 2019.
Mintel database entry for Bigen Permanent Powder Hair Colour (Jun. 2013).
Mintel database entry for Samy Fat Foam product (Oct. 2010).
Product Information for Maxton Bleach Powder, May 2006.
Statement of Grounds and Particulars AU (Australia) 2017251818 filed May 1, 2020.
Written Opinion for SG (Singapore) 11201609005Q dated May 5, 2020.
Third Party Observation filed in SG (Singapore) 11201609005Q dated Apr. 5, 2019.
Third Party Observation filed in SG (Singapore) 11201609005Q dated Dec. 27, 2018.
Third Party Observation filed in SG (Singapore) 11201609005Q dated Feb. 15, 2018.
Third Party Observation filed in SG (Singapore) 11201609005Q dated May 25, 2018.
Third Party Observation for SG (Singapore) 11201609005Q dated Dec. 8, 2017.
Third Party Observation for IL (Israel) 265590 dated Mar. 26, 2020.
Declaration by Dr. Hefford dated Jan. 7, 2020 filed in KR Appeal No. 2019Heo3618.
Declaration by Prof. Steve Rannard dated Dec. 25, 2019 filed in KR Appeal No. 2019Heo3618.
Declaration of Prof. Steve Rannard dated Oct. 27, 2019 filed in EP 15725209.9.
English Summary of Examination Report CN (China) 201480042200.1, dated Jan. 29, 2020.
English Summary of Examination Report QA (Qatar) QA/201601/00021, dated Dec. 12, 2019.
English Summary of Office Action HN (Honduras) 2016002313, dated Feb. 11, 2020.
English Summary of Office Action ID (Indonesia) P00 201608726, dated Oct. 17, 2019.
English Summary of Office Action MX (Mexico) MX/a/2016/014917, dated Feb. 25, 2020.
English Translation of Examination Report PE (Peru) 0001022016/DIN, dated Jan. 15, 2020.
Examination report regarding GB (Great Britain) 1605346.4, dated Nov. 13, 2018.
Examination report regarding GB (Great Britain) 1813313.2, dated Jan. 14, 2019.
KIPO Brief in Appeal of Cancellation Decision with English Translation dated Jan. 13, 2020.
Printout of the webpage http://www.olaplex.com/pages/patent, taken on Sep. 22, (2016).
Third Party Observation CA (Canada) 2947303, dated Jan. 14, 2020.
Notice of Opposition in European Application No. EP 16720308.2 with English Translation dated Jul. 14, 2020.

\* cited by examiner

METHODS AND FORMULATIONS FOR CURLING HAIR

CROSS-REFERENCE TO RELATED APPLICATIONS

This application is a continuation of pending U.S. application Ser. No. 15/640,044, filed Jun. 30, 2017, which was a continuation-in-part of U.S. application Ser. No. 15/282,792, filed Sep. 30, 2016, now U.S. Pat. No. 6,713,583, which claims priority to U.S. Provisional Application Ser. No. 62/361,366, filed Jul. 12, 2016, and to U.S. Provisional Application Ser. No. 62/380,020, filed Aug. 26, 2016, the disclosures of which are incorporated herein by reference in their entirety.

FIELD OF THE INVENTION

The present invention generally relates to formulations and methods for curling hair, particularly for imparting and controlling a level of curl to the hair.

BACKGROUND OF THE INVENTION

Hair consists of many long, parallel chains of amino acids. These chains, or polymers, of amino acids are bound to each other via 1) hydrogen bonding, 2) salt bridges between acid and base groups, and 3) disulfide bonds.

At alkaline pH, the disulfide bonds in hair can be broken (Dombrink et al., *Chem Matters*, 1983, page 8). For example, lye-based relaxers contain hydroxide ions which attack the disulfide linkages. The cleavage of disulfide bonds by the lye-based relaxer is used to achieve straightening of the hair through changing of the relative positions of polypeptide chains. The straightening process is completed by rinsing the hair and/or application of a neutralizing formulation.

While lye and other alkali-based relaxers are highly effective at relaxing and straightening hair, they can result in reduction of hair strength and potential loss of hair through breakage.

Additionally, it is well known that lye and alkali-based relaxers cannot be used to perm hair.

Traditional perms are performed using thiol based reducing agents followed by a second oxidizing step, typically using hydrogen peroxide, to set the hair. These thiol based reducing agents are foul smelling and if not properly rinsed between the steps can result in broken hair.

Thus, there is a need for hair curling formulations and treatments that can provide improved conditioning benefit for hair when the hair is curled. Specifically, there is a need to provide long lasting moisturized feel, smooth feel, and manageability control to curled hair.

There is also a need for hair curling formulations and treatments that afford the ability to tune or select the level of curl imparted to hair.

There is also a need for hair curling formulations and treatments that can be applied to the hair as a single formulation.

Additionally, there is a need for hair curling formulations without a foul thiol or related odor.

Therefore, it is an object of this invention to provide improved curling formulations and curling methods for repairing and/or strengthening curled hair.

It is a further object of this invention to provide curling formulations and methods which can be used to tune or select the level of curl imparted to hair.

It is a further object of this invention to provide hair curling formulations and treatments that can be applied to the hair as a single formulation, as well as formulations without a foul thiol-based odor.

SUMMARY OF THE INVENTION

Formulations, kits, and methods for curling hair are described which include the use of hydroxide-containing agents or formulations thereof in combination with the use of active agents or formulations thereof. The formulations, kits, and methods can also be used to control the level of curl imparted to the hair during the curling process. In certain embodiments, the formulation for curling hair may be applied one or more times after a hair curling treatment to change the level of curl in the hair.

The methods described herein include the step of reshaping hair prior to, during, or following the application of any formulation containing one or more active agents and/or one or more hydroxide-containing agents.

Active agent formulations, which contain one or more compounds that interact with keratin through one or more binding events (e.g., absorption, binding, etc.) and can also react with one or more nucleophiles, such as thiols, in the hair are described herein. "Binding" as used herein refers to the formation of covalent, ionic, or hydrogen bonds. The active agent formulations can also provide improved conditioning and provide long lasting moisturized and smooth feel without leaving the hair greasy, improve appearance (e.g., sheen), increase dry strength (tensile strength), ease combing of the hair when wet or dried, reduce hair breakage, or decrease frizz, or any combination thereof.

Traditional methods of curling hair do not use lye or alkali-based or hydroxide-containing agents, which are known hair relaxers/straighteners and which can result in reduction of hair strength and potential loss of hair through breakage. The curling methods disclosed herein apply to hair active agents in combination with hydroxide-containing agents (or formulations thereof). These methods curl hair and repair damage to the curled hair. Additionally, the curling methods described herein provide improved methods of styling hair, such as during a hair curling treatment.

It is believed that the use of the one or more active agents permits not only control of the level of curl imparted to hair during a hair curling process but further prevents damage caused by the hydroxide-containing agent(s) applied to the hair.

A combined formulation containing both the active agent and one or more hydroxide-containing agents is applied to the hair during a hair curling process or treatment. Alternatively an active agent formulation concurrently with a formulation containing one or more hydroxide-containing agents is applied during a hair curling process or treatment. The addition of the active agent(s) simultaneously with hydroxide-containing agents can be used to tune or control the level of curl imparted to hair during the curling process. The level of curl imparted can depend on the amount of active agent(s) used, which can be represented as a weight ratio of active agent present in the formulation or formulations applied to the hair to the amount of hydroxide-containing agent(s) present in a formulation applied to the hair during the hair curling process. Preferably the formulations are applied simultaneously; optionally they are mixed just prior to application to form a combined formulation. Alternatively, the active agent and hydroxide-containing agents may be provided as a single, pre-mixed combined formulation.

The pH of the combined formulation is preferably at least about 9.5, more preferably at least about 10.5. In some embodiments, the pH of the combined formulation is about 11 or greater. In some embodiments, the pH of the combined formulation is about 10 or greater. When the formulations are mixed at the time of use, preferably the amount of active agent formulation used does not lower the pH of the combined formulation to be below about a pH of 9.5 and more preferably does not lower the pH of the combined formulation below about a pH of 10.5.

The weight ratio of the hydroxide-containing agent formulation to the active agent formulation can be in the range of about 10:1 to about 1:5; 5:1 to 1:5; 4:1 to 1:4; or 3:1 to 1:3. In some embodiments, the weight ratio of the hydroxide-containing agent formulation to the active agent formulation is in the range of about 10:1 to about 1:1; 5:1 to 1:1; 4:1 to 1:1; or 3:1 to 1:1. In some instances, the weight ratio is about 10:1, 9:1, 8:1, 7:1, 6:1, 5:1, 4:1, 3:1, 2:1, 1:1, 1:2, 1:3, 1:4, or 1:5 or within about 10% of these ratios, preferably the weight ratio is about 5:1, 4:1, 3:1, 2:1, 1:1, 1:2, 1:3, 1:4, or 1:5 or within about 10% of these ratios.

In some other embodiments, the active agent formulations can be applied to the hair immediately following or shortly after (e.g. within 1-5 minutes) the application of the hydroxide-containing agents, or formulations thereof.

The curl imparted to the hair following a curling treatment method defined herein (referred to herein as "imparted curl") can be maintained with no appreciable or substantially no appreciable change for a period of time. The treated hair retains curl when subjected to conditions, such as one or more wash cycles, under which it would not retain the curl absent treatment according to the methods described herein.

In some embodiments, the percentage of curl is reduced by less than about 5%, 10%, 15%, 20%, or 50% of the imparted curl after about 1, 2, 3, 4, 5, 6, 7, 8, 9, 10, 15, 20, 25, 30, 35, 40, 45, or 50 or more wash cycles. In certain embodiments, the curl is retained with no appreciable or substantially no appreciable change after about 1, 2, 3, 4, 5, 6, 7, 8, 9, 10, 15, 20, 25, 30, 35, 40, 45, or 50 or more wash cycles.

DETAILED DESCRIPTION OF THE INVENTION

I. Definitions

Numerical ranges disclosed herein disclose individually each possible number in such range, as well as any sub-ranges and combinations of sub-ranges encompassed therein. For example, a carbon range (i.e., $C_1$-$C_{10}$) is intended to disclose individually every possible carbon value and/or sub-range encompassed within. For example, a carbon length range of $C_1$-$C_{10}$ discloses $C_1$, $C_2$, $C_3$, $C_4$, $C_5$, $C_6$, $C_7$, $C_8$, $C_9$, and $C_{10}$, as well as discloses sub-ranges encompassed within, such as $C_2$-$C_9$, $C_3$-$C_8$, $C_1$-$C_5$, etc. Similarly, an integer value range of 1-10 discloses the individual values of 1, 2, 3, 4, 5, 6, 7, 8, and 10, as well as sub-ranges encompassed within. Further, a concentration range or weight percent range, such as from 1% to 2% by weight of the formulation discloses, the individual values and fractions thereof, such as 1%, 1.1%, 1.2%, 1.32%, 1.48% etc. , as well as sub-ranges encompassed within.

The term "hair" refers to one or more than one strand of hair, as well as the natural components of hair, such as oil from a body. Hair also refers to virgin hair or processed hair, for example hair that has been exposed to hair waving or hair straightening formulations.

An "effective amount", e.g., of the active agent described herein, refers to an amount of the active agent in a formulation which, when applied as part of a desired hair treatment achieves the desired result, such as desired level of curl, smoothness, little or no breakage, great or good feel, and/or healthy appearance by visual inspection.

"Cosmetically acceptable" refers to those compounds, materials, and formulations, which are, within the scope of sound medical judgment, suitable for use in contact with the tissues of human beings and animals without excessive toxicity, irritation, allergic response, or other problems or complications commensurate with a reasonable benefit/risk ratio. More specifically, cosmetically acceptable refers to a material, compound, or formulation which is suitable for use in contact with the skin, scalp, or hair. Cosmetically acceptable materials are known to those of ordinary skill in the art.

"Shampoo", as used herein, generally refers to a liquid or semi-solid formulation applied to the hair that contains detergent or soap for washing the hair.

"Conditioner", as used herein, generally refers to a formulation (e.g., liquid, cream, lotion, gel, semi-solid) applied to the hair to soften the hair, smooth the hair, and/or change the sheen of the hair.

"Reshaping", as used herein, generally refers to a deformation, such as mechanical deformation of the hair including, but not limited to rolling, braiding, and/or twisting of the hair. Reshaping hair, however, is not intended to refer to a deformation that results in straightening hair or straightened hair.

"Analog" and "Derivative" are used herein interchangeably and refer to a compound that possesses the same core as the parent compound, but differs from the parent compound in bond order, the absence or presence of one or more atoms and/or groups of atoms, and combinations thereof. The derivative can differ from the parent compound, for example, in one or more substituents present on the core, which may include one or more atoms, functional groups, or substructures. In general, a derivative can be imagined to be formed, at least theoretically, from the parent compound via chemical and/or physical processes.

"Electrophilic group" or "electrophilic moiety" are used interchangeably and refer to one or more functional groups or moieties that have an affinity for or attract electrons.

"Michael acceptor", as used herein, is a species of electrophilic groups or moieties that participates in nucleophilic addition reactions. The Michael acceptor can be or can contain an α,β-unsaturated carbonyl-containing group or moiety, such as a ketone. Other Michael acceptors include pi-bonds, such as double or triple bonds conjugated to other pi-bond containing electron withdrawing groups, such as nitro groups, nitrile groups, and carboxylic acid groups or aryl groups.

"Alkyl", as used herein, refers to the radical of saturated or unsaturated aliphatic groups, including straight-chain alkyl, alkenyl, or alkynyl groups, branched-chain alkyl, alkenyl, or alkynyl groups, cycloalkyl, cycloalkenyl, or cycloalkynyl (alicyclic) groups, alkyl substituted cycloalkyl, cycloalkenyl, or cycloalkynyl groups, and cycloalkyl substituted alkyl, alkenyl, or alkynyl groups. Unless otherwise indicated, a straight chain or branched chain alkyl has 30 or fewer carbon atoms in its backbone (e.g., $C_1$-$C_{30}$ for straight chain, $C_3$-$C_{30}$ for branched chain), more preferably 20 or fewer carbon atoms, more preferably 12 or fewer carbon atoms, and most preferably 8 or fewer carbon atoms. In some embodiments, the chain has 1-6 carbons. Likewise, preferred cycloalkyls have from 3-10 carbon atoms in their ring structure, and more preferably have 5, 6 or 7 carbons in the ring structure. The ranges provided above are inclusive of all values between the minimum value and the maximum value.

The term "alkyl" includes both "unsubstituted alkyls" and "substituted alkyls", the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, a phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls.

The alkyl groups may also contain one or more heteroatoms within the carbon backbone. Examples include oxygen, nitrogen, sulfur, and combinations thereof. In certain embodiments, the alkyl group contains between one and four heteroatoms.

"Alkenyl" and "Alkynyl", as used herein, refer to unsaturated aliphatic groups containing one or more double or triple bonds analogous in length (e.g., $C_2$-$C_{30}$) and possible substitution to the alkyl groups described above.

"Aryl", as used herein, refers to 5-, 6- and 7-membered aromatic rings. The ring may be a carbocyclic, heterocyclic, fused carbocyclic, fused heterocyclic, bicarbocyclic, or biheterocyclic ring system, optionally substituted as described above for alkyl. Broadly defined, "Ar", as used herein, includes 5-, 6- and 7-membered single-ring aromatic groups that may include from zero to four heteroatoms. Examples include, but are not limited to, benzene, pyrrole, furan, thiophene, imidazole, oxazole, thiazole, triazole, pyrazole, pyridine, pyrazine, pyridazine and pyrimidine. Those aryl groups having heteroatoms in the ring structure may also be referred to as "heteroaryl", "aryl heterocycles", or "heteroaromatics". The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, and —CN. The term "Ar" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocycles, or both rings are aromatic.

"Alkylaryl", as used herein, refers to an alkyl group substituted with an aryl group (e.g., an aromatic or hetero aromatic group).

"Heterocycle" or "heterocyclic", as used herein, refers to a cyclic radical attached via a ring carbon or nitrogen of a monocyclic or bicyclic ring containing 3-10 ring atoms, and preferably from 5-6 ring atoms, containing carbon and one to four heteroatoms each selected from non-peroxide oxygen, sulfur, and N(Y) wherein Y is absent or is H, O, ($C_{1-4}$) alkyl, phenyl or benzyl, and optionally containing one or more double or triple bonds, and optionally substituted with one or more substituents. The term "heterocycle" also encompasses substituted and unsubstituted heteroaryl rings. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl.

"Heteroaryl", as used herein, refers to a monocyclic aromatic ring containing five or six ring atoms containing carbon and 1, 2, 3, or 4 heteroatoms each selected from non-peroxide oxygen, sulfur, and N(Y) where Y is absent or is H, O, ($C_1$-$C_8$) alkyl, phenyl or benzyl. Non-limiting examples of heteroaryl groups include furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide), quinolyl (or its N-oxide) and the like. The term "heteroaryl" can include radicals of an ortho-fused bicyclic heterocycle of about eight to ten ring atoms derived therefrom, a derivative derived by fusing a propylene, trimethylene, or tetramethylene diradical thereto. Examples of heteroaryl include, but are not limited to, furyl, imidazolyl, triazolyl, triazinyl, oxazoyl, isoxazoyl, thiazolyl, isothiazoyl, pyraxolyl, pyrrolyl, pyrazinyl, tetrazolyl, pyridyl (or its N-oxide), thientyl, pyrimidinyl (or its N-oxide), indolyl, isoquinolyl (or its N-oxide), quinolyl (or its N-oxide), and the like.

"Halogen", as used herein, refers to fluorine, chlorine, bromine, or iodine.

The term "substituted" as used herein, refers to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, aminoacid, peptide, and polypeptide groups.

Heteroatoms, such as nitrogen, may have hydrogen substituents and/or any permissible substituents of organic compounds described herein that satisfy the valences of the heteroatoms. It is understood that "substitution" or "substituted" includes the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc.

"Polymer", as used herein, refers to a molecule containing more than 10 monomer units.

"Water-soluble", as used herein, generally means at least 50, 75, 100, 125, 150, 200, 225, or 250 g is soluble in 1 L of water at 25° C.

"Hydroxide-containing agents," as used herein, typically refers to hydroxide-containing compounds that are commonly used in current hair relaxing formulations, such as lye or other hydroxide-containing compounds, such as ammonium hydroxide. When these hydroxide-containing compounds are present in a hair curling formulation, the hydroxide ions produce a formulation with a high pH, such as pH ranging from 10 to 14, preferably a pH ranging from 12 to 14.

"Lye agents" or "alkali-based agents" are used interchangeably herein and refer to alkali metal containing hydroxides (e.g. sodium hydroxide and/or potassium hydroxide).

II. Active Agent Formulations

The active agent formulations disclosed herein are used in methods for curling hair in combination with a hydroxide-containing agent(s) or a formulation thereof. Additionally, the active agent formulations, when used during the curling process/treatment can be used to control, select, or tune the level of curl imparted to the hair, as compared to the hair's natural state. The level of curl imparted depends on the amount of one or more active agents applied, which can be represented as a weight ratio of the weight of one or more active agents (or the weight of the active agent formulation) to the weight of the hydroxide-containing formulation. Furthermore, the inclusion of one or more active agents reduces hair breakage and damage during the curling process.

The formulations contain one or more active agents (also referred to herein as "compounds" or "active agents"), which can be combined with one or more cosmetically acceptable carriers and/or excipients that are considered safe and effective to apply to human hair and/or the human scalp, and may be administered to an individual's hair without causing undesirable biological side effects, such as burning, itching, and/or redness, or a similar adverse reaction.

The active agent is typically present in the formulation in an amount ranging from about 0.05 wt % to about 25 wt % of the formulation, such as from about 0.1 wt % to about 10 wt %, from about 0.1 wt % to about 4 wt %, or from about 0.5 wt % to 3 wt %. Typically, the active agent may be present in the formulation in an amount ranging from about 0.5 wt % to about 5 wt % of the formulation.

The active agent is stable in aqueous solution for a period of at least 2, 3, 4, 5, 6, 8, 9, 10, 11, or 12 months or longer at a pH of 3 to 8, preferably at a pH of 3 to 5, and at a temperature of about 25-30° C., preferably about 25° C. "Stable" as used herein with respect to shelf-life means that at least 40, 45, 50, 55, 60, 65, 70, 75, 80, 85, 90, or 95% of the active agent(s) is unchanged over the specified time period.

The active agent formulation generally does not contain a strong base, such as a nitrogen containing base (e.g. guanadine, amidine, or a derivative thereof).

A. Active Agent

The active agent contains at least one reactive moiety capable of reacting with and forming bonds with a nucleophile, such as a thiol or amine. The active agent optionally contains a linker group. The active agent can contain one or more acidic groups, such as carboxylic acids, sulfonic acids, phosphonic acids.

Without being bound by theory, it is believed that the reactive moieties, upon reaction with nucleophiles, such as thiol groups, on the hair follicle, form bonds that are stable, for example, hydrolytically stable. "Stable", as used in reference to the bonds formed in the hair follicles means the bonds remain intact for at least one week, two weeks, three weeks, four weeks, one month, or two months or longer when exposed to water at a pH of 3 to 8, preferably at a pH of 3 to 5, at a temperature from about 5° C. to about 100° C., from about 20° C. to about 75° C., more preferably from about 20° C. to about 50° C., from about 25° C. to about 40° C., or from about 25° C. to about 30° C., and more preferably at a temperature of about 25° C.

It is preferred that the reaction between the reactive moieties and thiols occurs around room temperature, for example, from about 15° C. to about 35° C., preferably from about 20° C. to about 30° C., more preferably from about 22° C. to about 27° C.

1. Active Agents Defined by Formula I

In some embodiments, the active agents have a structure according to Formula I:

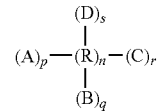

Formula I wherein
A, B, C, and D are reactive moieties containing one or more charges,
R is a linker that contains two or more charges, wherein the charges are opposite to the charges on the reactive moieties, wherein n=1-100, preferably n=1-10, more preferably n=1; and each occurrence of p, q, r, and s is independently an integer from 0 to 25, preferably from 0 to 10, more preferably from 0 to 2. The sum of p+q+r+s is equal to or greater than 2.

The reactive moieties may be present on any atom of the linker. In some embodiments, the reactive moieties are the same. In some embodiments, one or more of the reactive moieties is different.

In some embodiments, the reactive moieties are negatively charged and the linker has positively charged moieties. In other embodiments, the reactive moieties are positively charged and the linker has negatively charged moieties. Generally, the sum of the charges on the active agent of Formula I is zero, although stoichiometric imbalances may exist.

The reactive moieties on the active agents of Formula I are preferably linked via a linker R. The linker R, as used herein, refers to one or more polyfunctional, e.g. bifunctional molecules, trifunctional molecules, tetrafunctional molecules, etc., which can be used to ionically bind the two or more reactive moieties and which do not interfere with the reactive properties of the active agents. The reactive moieties may be attached to any part of linker R.

a. Linker R

In a preferred embodiment, in Formula I, n=1 and the linker R is not a polymer. The linker R can be a single atom, such as a heteroatom (e.g., O or S), a group of atoms, such as a functional group (e.g., amine, —C(=O)—, —CH$_2$—), or multiple groups of atoms, such as an alkylene chain. Suitable linkers include but are not limited to oxygen, sulfur, carbon, boron, nitrogen, alkoxy, alkyl, alkenyl, cycloalkyl, cycloalkenyl, aryl, heterocycloalkyl, heteroaryl, ether, amine, and an oligomer.

The linker R is optionally independently substituted with one or more substituents including hydrogen, halogen, cyano, alkoxy, alkyl, alkenyl, cycloalkyl, cycloalkenyl, aryl, heterocycloalkyl, heteroaryl, amine, hydroxy, formyl, acyl, carboxylic acid (—COOH), —C(O)R$^1$, —C(O)OR$^1$, carboxylate (—COO$^-$), primary amide (e.g., —CONH$_2$), secondary amide, —C(O)NR$^1$R$^2$, —NR$^1$R$^2$, —NR$^1$S(O)$_2$R$^2$, —NR$^1$C(O)R$^2$, —S(O)$_2$R$^2$, —SR$^1$, and —S(O)$_2$NR$^1$R$^2$, sulfinyl group (e.g., —SOR$^1$), and sulfonyl group (e.g., —SOOR$^1$); wherein R$^1$ and R$^2$ may each independently be hydrogen, alkyl, alkenyl, alkynyl, cycloalkyl, aryl, heterocycloalkyl and heteroaryl; wherein each of R$^1$ and R$^2$ is optionally independently substituted with one or more substituents selected from the group consisting of halogen, hydroxyl, cyano, nitro, amino, alkylamino, dialkylamino, alkyl optionally substituted with one or more halogen or alkoxy or aryloxy, aryl optionally substituted with one or more halogen or alkoxy or alkyl or trihaloalkyl, heterocycloalkyl optionally substituted with aryl or heteroaryl or =O, or alkyl optionally substituted with hydroxyl, cycloalkyl optionally substituted with hydroxyl, heteroaryl optionally substituted with one or more halogen or alkoxy or alkyl or trihaloalkyl, haloalkyl, hydroxyalkyl, carboxy, alkoxy, aryloxy, alkoxycarbonyl, aminocarbonyl, alkylaminocarbonyl and dialkylaminocarbonyl.

In some embodiments, the linker R may be an alkoxy, ether, alkyl, alkenyl, cycloalkyl, cycloalkenyl, aryl, heterocycloalkyl, heteroaryl, or amine.

b. Active Agents According to Formula I

The active agent according to Formula I contains at least two reactive moieties that are capable of reacting with a nucleophile, such as a thiol or amine, to form covalent bonds. For example, the reactive moieties are capable of reacting with a thiol group in the hair to form a stable covalent bond. The reactive moiety is typically an electrophilic moiety capable of forming a salt with the linker. Alternately, the reactive moiety can be capable of reacting with a free radical.

The active agent according to Formula I contains at least two reactive moieties. However, the active agent may contain three, four, five, six, or greater than six reactive moieties.

The reaction between the reactive moiety and the thiol groups may be initiated at room temperature and pressure when the reactive moiety contacts a thiol group in the hair. In some embodiments, the reaction may require an initiator, such as heat, catalyst, basic conditions, or a free radical initiator. The rate of reaction between the reactive moiety and the thiol may be increased by changes in temperature, pH, and/or addition of one or more excipients, such as a catalyst; however, this is generally not required.

The two or more reactive moieties on the active agent can be the same. In some embodiments, the two or more reactive moieties are different.

In some embodiments, the reactive moieties are capable of undergoing a conjugate additional reaction. The reactive moieties can independently be or contain a Michael acceptor, a succinimidyl-containing group, a maleimido-containing group, azlactone, a benzoxazinone derivative, vinyl sulfone, vinyl sulfoximine, vinyl sulfonate, vinyl phosphonate, benzoxazinone, isocyanate, epoxide, an electrophilic moiety containing a leaving group, an electrophilic thiol acceptor, acrylic or acrylate group, a methacrylic or methacrylate group, a styrene group, an acryl amide group, a methacryl amide group, a maleate group, a fumarate group, an itaconate group, a vinyl ether group, an allyl ether group, an allyl ester group, a vinyl ester group, a sulfonate group, a phosphonate group, a sulfoxide group, a sulfonamide group, a sulfinimide group, a sulfinamide group, a sulfonimidate group, or a sulfonimidamide group.

In the preferred embodiments, each of reactive moieties A, B, C, and/or D when present independently contains a moiety selected from the group consisting of a vinyl sulfone, an acrylate group, a methacrylate group, a styrene group, an acryl amide group, a methacryl amide group, a maleate group, a fumarate group, and an itaconate group. Further, in the preferred embodiments, n=1 and the linker R is not a polymer. Optionally, all of the reactive moieties are the same. For example, in some embodiments all of the reactive moieties are maleate groups.

In some embodiments, the active agent according to Formula I has one of the following structures:

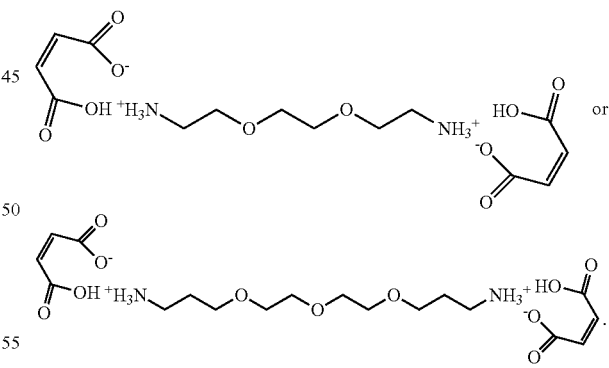

Active agents according to Formula I are further described in U.S. Pat. No. 9,095,518, which is incorporated herein by reference with respect to its disclosure of active agents.

2. Active Agents Defined by Formula II

In some other embodiments, the active agent is a polyfunctional compound that contains ionizable functional groups capable of forming ionic bonds and functional groups capable of forming a covalent bond with a nucleophile, such as a thiol or an amine.

The active agent may have the following Formula II:

wherein Z is a linker or is absent, m and n are each an integer independently selected from 1-6, provided that m+n is at least 2, B is a functional group capable of forming a covalent bond with a thiol or amine group, and A is an ionizable functional group. Preferably, the linker Z is not a polymer. Optionally, the active agent is a simple salt of Formula II.

Suitable ionizable functional groups (group A) include, but are not limited to, acidic groups such as carboxylic acids, sulfonic acids, phosphonic acids, and basic groups, such as amines.

Suitable functional groups capable of forming a covalent bond with a nucleophile, such as a thiol or an amine, (group B) include, but are not limited to, Michael acceptors, alkyl halides or sulfonate esters. Exemplary active agents according to Formula II may contain thiol reactive functional groups, as group B, for example, such as those shown in the following moieties:

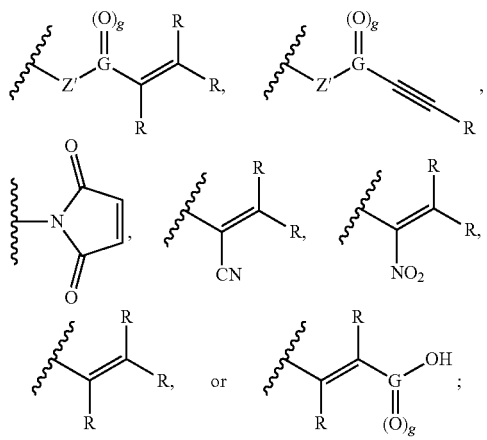

wherein R is independently selected from hydrogen, $C_{1-6}$ alkyl, aryl, or an ionizable functional group; Z' is oxygen (O), NH, or is absent; and G is carbon (C) and g is 1, or G is sulfur (S) and g is 2. In preferred embodiments, Z is a linker or is absent, the linker is not a polymer, and group B is a functional group capable of forming a covalent bond with a thiol or amine group and group B is independently selected from the group consisting of:

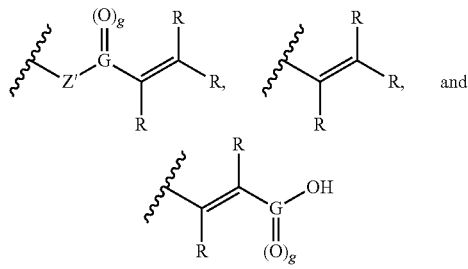

wherein R, Z', G, and g are as previously defined.

a. Linker Z of Formula II

The linker Z, when present, can be or can contain an alkyl, alkenyl, cycloalkyl, cycloalkenyl, aryl, heterocycloalkyl or heteroaryl group. One or more of the carbon atoms in the alkyl, alkenyl, cycloalkyl, cycloalkenyl, and aryl groups can be substituted with a heteroatom, yielding, for instance, an ether or alkylamine-containing linker.

The linker Z may be substituted with one or more substituents, which may be the same or different, including hydrogen, halogen, cyano, alkoxy, alkyl, alkenyl, cycloalkyl, cycloalkenyl, aryl, heterocycloalkyl, heteroaryl, amine, hydroxy, oxo, formyl, acyl, carboxylic acid (—COOH), —C(O)R$^1$, —C(O)OR$^1$, carboxylate (—COO—), primary amide (e.g., —CONH$_2$), secondary amide, —C(O)NR$^1$R$^2$, —NR$^1$R$^2$, —NR$^1$S(O)$_2$R$^2$, —NR$^1$C(O)R$^2$, —S(O)$_2$R$^2$ , —SR$^1$, and —S(O)$_2$NR$^1$R$^2$, sulfinyl group (e.g., —SOR$^1$), and sulfonyl group (e.g., —SOOR$^1$); wherein R$^1$ and R$^2$ may each independently be hydrogen, alkyl, alkenyl, alkynyl, cycloalkyl, aryl, heterocycloalkyl and heteroaryl; wherein each of R$^1$ and R$^2$ is optionally independently substituted with one or more substituents selected from the group consisting of halogen, hydroxyl, oxo, cyano, nitro, amino, alkylamino, dialkylamino, alkyl optionally substituted with one or more halogen or alkoxy or aryloxy, aryl optionally substituted with one or more halogen or alkoxy or alkyl or trihaloalkyl, heterocycloalkyl optionally substituted with aryl or heteroaryl or oxo, or alkyl optionally substituted with hydroxyl, cycloalkyl optionally substituted with hydroxyl, heteroaryl optionally substituted with one or more halogen or alkoxy or alkyl or trihaloalkyl, haloalkyl, hydroxyalkyl, carboxy, alkoxy, aryloxy, alkoxycarbonyl, aminocarbonyl, alkylaminocarbonyl, and dialkylaminocarbonyl.

In certain preferred embodiments, the linker Z is a $C_{1-10}$ io alkyl group which may be unsubstituted or substituted one or more times by oxo, hydroxyl, carboxyl, amido or amino. Preferably, the linker Z is a $C_{1-4}$ alkyl group. The alkyl group may be linear or branched. The alkyl group may also be interrupted one or more times by a heteroatom selected from oxygen, sulfur and nitrogen. An example of such a dicarboxylic acid having a heteroatom interruption is thiodipropionic acid. In other embodiments, the alkyl group may contain one or more double or triple bonds.

In some embodiments, the active agent according to Formula II has one of the following structures:

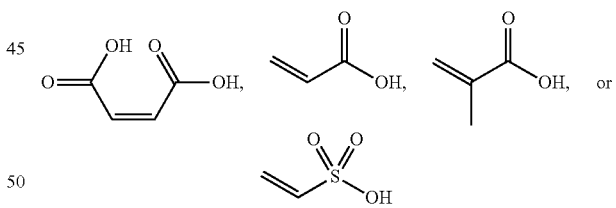

or is a simple salt of these structures.

The term "simple salt," as used herein, refers to a salt formed from the ionized form of an active agent of Formula II with a counterion group having a charge opposite to the charge of the ionizable functional group A. In preferred embodiments, a simple salt includes only one active agent and one counterion group. The counterion group can be a suitable ionized metal or an optionally substituted $C_1$-$C_{10}$, $C_1$-$C_8$, or $C_1$-$C_6$ alkyl, $C_2$-$C_{10}$, $C_2$-$C_8$, or $C_2$-$C_6$ alkenyl, or $C_2$-$C_{10}$, $C_2$-$C_8$, or $C_2$-$C_6$ alkynyl counterion group covalently bound to an ionic moiety. For example, if the ionizable functional group A has a negative charge (e.g., —C(O)O$^-$), then the counterion group has a positive charge (e.g. aminium group). The $C_1$-$C_{10}$, $C_1$-$C_8$, or $C_1$-$C_6$ alkyl, $C_2$-$C_{10}$, $C_2$-$C_8$, or $C_2$-$C_6$ alkenyl, or $C_2$-$C_{10}$, $C_2$-$C_8$, or $C_2$-$C_6$ alkynyl counterion groups may be substituted one or more times by substituents as defined above with respect to linker Z. Optionally substituted $C_3$-$C_{10}$, $C_3$-$C_8$, or $C_3$-$C_6$ alkyl counterion groups may be linear, branched, or cyclic. The $C_1$-$C_{10}$, $C_1$-$C_8$, or $C_1$-$C_6$ alkyl, $C_2$-$C_{10}$, $C_2$-$C_8$, or $C_2$-$C_6$ alkenyl, or $C_2$-$C_{10}$, $C_2$-$C_8$, or $C_2$-$C_6$ alkynyl counterion groups may also be interrupted one or more times along the backbone by a heteroatom selected from oxygen, sulfur, and/or nitrogen. In certain embodiments, the counterion groups do not contain a carbon-carbon double bond. In certain other embodiments, the counterion groups have a molecular weight of less than about 200 g/mol, 150 g/mol, 125 g/mol, 100 g/mol, 100 g/mol, 90 g/mol, 80 g/mol, 70 g/mol, 60 g/mol, 50 g/mol, 40 g/mol, 30 g/mol, or 20 g/mol.

Exemplary counterion groups include, but are not limited to, sodium ion, potassium ion, ethanolammonium, and allylammonium.

3. Active Agents Defined by Formula III

In certain embodiments, when the active agent of Formula II is a simple salt it can have a structure according to Formula III:

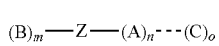

Formula III wherein Z is a linker or is absent, m and n are each an integer independently selected from 1-6, provided that m+n is at least 2, B is a functional group capable of forming a covalent bond with a nucleophile, such as a thiol or amine group, A is an ionizable functional group as defined above, and C is an ionic group which is also capable of forming a covalent bond with a thiol and which has a charge opposite to that of ionizable group A. Group C is ionically bonded (denoted by dashed line) to group A. For ionic group C, o is an integer value independently selected from 1-6, such that the sum of charges of group C and ionizable group A is zero. Preferably, linker Z is not a polymer.

In active agents of Formula III, group C is an ionic group which is ionically bonded to ionizable group A and is also capable of forming a covalent bond with a thiol. Group C may be a Michael acceptor, a succinimidyl-containing group, a maleimido-containing group, azlactone, a benzoxazinone derivative, vinyl sulfone, vinyl sulfoximine, vinyl sulfonate, vinyl phosphonate, benzoxazinone, isocyanate, epoxide, an electrophilic moiety containing a leaving group, an electrophilic thiol acceptor, acrylic or acrylate group, a methacrylic or methacrylate group, a styrene group, an acryl amide group, a methacryl amide group, a maleate group, a fumarate group, an itaconate group, a vinyl ether group, an allyl ether group, an allyl ester group, a vinyl ester group, a sulfonate group, a phosphonate group, a sulfoxide group, a sulfonamide group, a sulfinimide group, a sulfinamide group, a sulfonimidate group, or a sulfonimidamide group. By way of example, group C can be an allylammonium or 2-(methacrylolyoxy)ethan-l-ammonium.

The active agents according to Formula III may contain thiol reactive functional groups which react with a nucleophile, such as a thiol, as group B. Examplary thiol reactive functional groups include, but are not limited to, those shown in the following moieties:

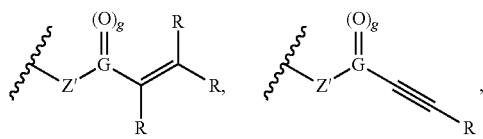

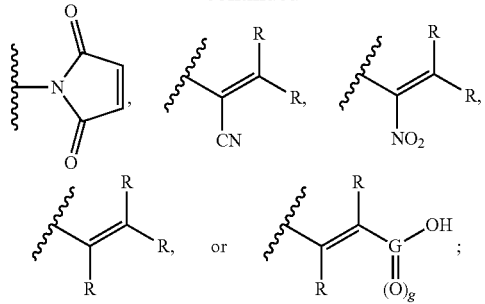

wherein R is independently selected from hydrogen, $C_{1-6}$ alkyl, aryl, or an ionizable functional group; Z' is oxygen (O), NH, or is absent; and G is carbon (C) and g is 1, or G is sulfur (S) and g is 2. In preferred embodiments, Z is a linker or is absent, the linker is not a polymer, and group B is a functional group capable of forming a covalent bond with a thiol or amine group and group B is independently selected from the group consisting of:

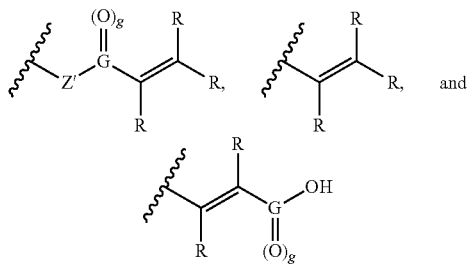

wherein R, Z', G, and g are as previously defined.

a. Linker Z of Formula III

The linker Z, when present, can be or can contain an alkyl, alkenyl, cycloalkyl, cycloalkenyl, aryl, heterocycloalkyl or heteroaryl group. One or more of the carbon atoms in the alkyl, alkenyl, cycloalkyl, cycloalkenyl, and aryl groups can be substituted with a heteroatom, yielding, for instance, an ether or alkylamine-containing linker.

The linker Z may optionally be substituted with one or more substituents, which may be the same or different, including hydrogen, halogen, cyano, alkoxy, alkyl, alkenyl, cycloalkyl, cycloalkenyl, aryl, heterocycloalkyl, heteroaryl, amine, hydroxy, oxo, formyl, acyl, carboxylic acid (—COOH), —C(O)R$^1$, —C(O)OR$^1$, carboxylate (—COO—), primary amide (e.g., —CONH$_2$), secondary amide, —C(O)NR$^1$R$^2$, —NR$^1$R$^2$, —NR$^1$S(O)$_2$R$^2$, —NR$^1$C(O)R$^2$, —S(O)$_2$R$^2$, —SR$^1$, and —S(O)$_2$NR$^1$R$^2$, sulfinyl group (e.g., —SOR$^1$), and sulfonyl group (e.g., —SOOR$^1$); wherein R$^1$ and R$^2$ may each independently be hydrogen, alkyl, alkenyl, alkynyl, cycloalkyl, aryl, heterocycloalkyl and heteroaryl; wherein each of R$^1$ and R$^2$ is optionally independently substituted with one or more substituents selected from the group consisting of halogen, hydroxyl, oxo, cyano, nitro, amino, alkylamino, dialkylamino, alkyl optionally substituted with one or more halogen or alkoxy or aryloxy, aryl optionally substituted with one or more halogen or alkoxy or alkyl or trihaloalkyl, heterocycloalkyl optionally substituted with aryl or heteroaryl or oxo or alkyl optionally substituted with hydroxyl, cycloalkyl optionally substituted with hydroxyl, heteroaryl optionally substituted with one or more halogen or alkoxy or alkyl or trihaloalkyl, haloalkyl, hydroxyalkyl, carboxy, alkoxy, aryloxy, alkoxycarbonyl, aminocarbonyl, alkylaminocarbonyl, and dialkylaminocarbonyl.

In certain preferred embodiments, the linker Z is a $C_{1-10}$ alkyl group which may be unsubstituted or substituted one or more times by oxo, hydroxyl, carboxyl, amido or amino. Preferably, the linker Z is a $C_{1-4}$ alkyl group. The alkyl group may be linear or branched. The alkyl group may also be interrupted one or more times by a heteroatom selected from oxygen, sulfur and nitrogen. An example of such a dicarboxylic acid having a heteroatom interruption is thiodipropionic acid. In other embodiments, the alkyl group may contain one or more double or triple bonds.

In some embodiments, the active agent of Formula III has one of the following structures:

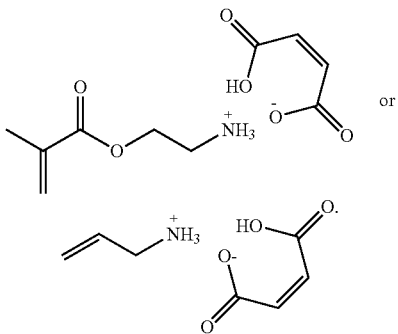

B. Excipients Active agent formulations typically contain one or more cosmetically acceptable excipients. Cosmetically acceptable excipients include, but are not limited to, water, preservatives, antioxidants, chelating agents, sunscreen agents, vitamins, dyes, hair coloring agents, proteins, amino acids, natural extracts such as plant extracts, humectants, fragrances, perfumes, oils, emollients, lubricants, butters, penetrants, thickeners, viscosity modifiers, polymers, resins, hair fixatives, film formers, surfactants, detergents, emulsifiers, opacifying agents, volatiles, propellants, liquid vehicles, carriers, salts, pH adjusting agents (e.g., citric acid), neutralizing agents, buffers, hair conditioning agents, anti-static agents, anti-frizz agents, anti-dandruff agents, absorbents, and combinations thereof.

In certain embodiments, the active agent formulations are free of thickeners or substantially free of thickeners (i.e. viscosity increasing agents).

The formulations may contain one or more cosmetically acceptable excipients. In some forms, the formulations contain the active agent, water, and optionally a preservative and/or fragrance.

The formulation for curling hair during or immediately following application of a hydroxide-containing formulation may be in any suitable physical form. Suitable forms include, but are not limited to low to moderate viscosity liquids, lotions, milks, mousses, sprays, gels, creams, shampoos, conditioners, and the like. Suitable excipients, such as those listed above, are included or excluded from the formulation depending on the form of the formulation (e.g., liquid, hair spray, cream).

The cosmetically acceptable excipient is typically present in an amount ranging from about 10 wt % to about 99.99 wt % of the formulation, preferably about 40 wt % to about 99 wt %, more preferably from about 80 wt % to about 99 wt %.

1. Surfactants

Surfactants are surface-active agents that are able to reduce the surface tension of water and cause the formulation to slip across or onto the hair. Surfactants may also include detergents and soap. The surfactants may be amphoteric, anionic, or cationic. Suitable surfactants that may be used in the formulation include, but are not limited to, 3-aminopropane sulfonic acid, almond amide, almond amidopropyl betaine, almond amidopropylamine oxide, aluminum hydrogenated tallow glutamate, aluminum lanolate, aminoethyl sulfate, aminopropyl lauryl glutamine, ammonium $C_{12-15}$ alkyl sulfate, ammonium $C_{12-15}$ pareth sulfate, ammonium $C_{12-16}$ alkyl sulfate, ammonium $C_{9-10}$ perfluoroalkylsulfonate, ammonium capryleth sulfate, ammonium capryleth-3 sulfate, ammonium monoglyceride sulfate, ammonium sulfate, ammonium isothionate, ammonium cocoyl sarcosinate, ammonium cumene sulfonate, ammonium dimethicone copolyol sulfate, ammonium dodecylbenzenesulfonate, ammonium isostearate, ammonium laureth sulfate, ammonium laureth-12 sulfate, ammonium laureth-5 sulfate, ammonium laureth-6 carboxylate, ammonium laureth-7 sulfate, ammonium laureth-8 carboxylate, ammonium laureth-9 sulfate, ammonium lauroyl sarcosinate, ammonium lauryl sulfate, ammonium lauryl sulfosuccinate, ammonium myreth sulfate, ammonium myristyl sulfate, ammonium nonoxynol-30 sulfate, ammonium nonoxynol-4 sulfate, ammonium oleate, ammonium palm kernel sulfate, ammonium polyacrylate, ammonium stearate, ammonium tallate, ammonium xylene sulfonate, ammonium xylene sulfonate, amp-isostearoyl gelatin/keratin amino acids/lysine hydroxypropyltrimonium chloride, amp-isostearoyl hydrolyzed collagen, apricot kernel oil PEG-6 esters, apricot amide, apricot amidopropyl betaine, arachideth-20, avocadamide, avocadamidopropyl betaine, babassuamide, babas suamidopropyl betaine, babas suamidopropylamine oxide, behenalkonium chloride, behenamide, behenamidopropyl betaine, behenamine oxide, sodium laureth sulfate, sodium lauryl sulfate, a polyoxyether of lauryl alcohol or ceteareth-20, or combinations thereof.

Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-.beta.-alanine, sodium N-lauryl-β-iminodipropionate, myristoamphoacetate, lauryl betaine and lauryl sulfobetaine.

More than one surfactant may be included in the formulation.

The surfactants are optionally included in an amount ranging from about 0.1% to about 15% by weight of the formulation, preferably about 1% to about 10% by weight of the formulation.

2. Emollients

Emollient refers to a material that protects against wetness or irritation, softens, soothes, coats, lubricates, moisturizes, protects, and/or cleanses the skin. Suitable emollients for use in the formulations include, but are not limited to a silicone compound (e.g., dimethicone, cyclomethicone, dimethicone copolyol or a mixture of cyclopentasiloxane and dimethicone/vinyldimethicone cross polymer, cyclopentasiloxane polysilicone), polyols such as sorbitol, glycerin, propylene glycol, ethylene glycol, polyethylene glycol, caprylyl glycol, polypropylene glycol, 1,3-butane diol, hexylene glycol, isoprene glycol, xylitol; ethylhexyl palmitate; a triglyceride such as caprylic/capric triglyceride and fatty acid ester such as cetearyl isononanoate or cetyl palmitate. In a specific embodiment, the emollient is dimethicone, amidodimethicone, dimethiconol, cyclopentasiloxane, potassium dimethicone PEG-7 panthenyl phosphate, or a combination thereof. More than one emollient may be included in the formulation.

The emollient is optionally included in an amount ranging from about 0.5% to about 15% by weight of the formulation, preferably from about 1% to about 10% by weight of the formulation.

3. Emulsifiers

The formulations may also contain one or more emulsifiers. Suitable emulsifiers include, but are not limited to, copolymers of an unsaturated ester and styrene sulfonate monomer, cetearyl alcohol, glyceryl ester, polyoxyethylene glycol ether of cetearyl alcohol, stearic acid, polysorbate-20, ceteareth-20, lecithin, glycol stearate, polysorbate-60, or polysorbate-80, or combinations thereof. More than one emulsifier may be included in the formulation.

The emulsifier is optionally included in an amount ranging from about 0.05% to about 15% by weight of the formulation, preferably from about 0.1% to about 10% by weight of the formulation.

4. Preservatives

One or more preservatives may be included in the formulations to prevent microbial growth in the formulations. Suitable preservatives include, but are not limited to, glycerin containing compounds (e.g., glycerin or ethylhexylglycerin or phenoxyethanol), benzyl alcohol, parabens (methylparaben, ethylparaben, propylparaben, butylparaben, isobutylparaben, etc.), sodium benzoate, ethylenediaminetetraacetic acid (EDTA), potassium sorbate, and/or grapefruit seed extract, or combinations thereof. More than one preservative may be included in the formulation. Other preservatives are known in the cosmetics industries and include salicylic acid, DMDM Hydantoin, Formaldehyde, Chlorphenism, Triclosan, Imidazolidinyl Urea, Diazolidinyl Urea, Sorbic Acid, Methylisothiazolinone, Sodium Dehydroacetate, Dehydroacetic Acid, Quaternium-15, Stearalkonium Chloride, Zinc Pyrithione, Sodium Metabisulfite, 2-Bromo-2-Nitropropane, Chlorhexidine Digluconate, Polyaminopropyl biguanide, Benzalkonium Chloride, Sodium Sulfite, Sodium Salicylate, Citric Acid, Neem Oil, Essential Oils (various), Lactic Acid, and Vitamin E (tocopherol).

The preservative is optionally included in an amount ranging from about 0.1% to about 5% by weight of the formulation, preferably from about 0.3% to about 3% by weight of the formulation. Preferably, the formulations are paraben free.

5. Conditioning Agents

One or more conditioning agents may be included in the formulations. Suitable conditioning agents include, but are not limited to, silicone-based agents (e.g., silicone quaternium-8), panthenol, hydrolyzed wheat and/or soy protein, amino acids (e.g. wheat amino acids), rice bran wax, meadowfoam seed oil, mango seed oil, grape seed oil, jojoba seed oil, sweet almond oil, hydroxyethyl behenamidopropyl dimonium chloride, aloe leaf extract, aloe barbadensis leaf juice, phytantriol, panthenol, retinyl palmitate, behentrimonium methosulfate, cyclopentasiloxane, quaternium-91, stearamidopropyl dimethylamine, and combinations thereof.

The conditioning agent(s) is optionally included in an amount ranging from about 0.01% to about 5% by weight of the formulation, preferably from about 0.05% to about 3% by weight of the formulation.

6. Diluents

Diluent, as used herein, refers to a substance(s) that dilutes the active agent. Water is the preferred diluent. The formulations typically contain greater than one percent (wt) water, preferably greater than five percent (wt) water, more preferably greater than 50% (wt) water, and most preferably greater than 80% (wt)water. Alcohols, such as ethyl alcohol and isopropyl alcohol, may be used at low concentrations (about 0.5% by weight of the formulation) to enhance hair or skin penetration and/or reduce odor.

7. Viscosity Modifying Agents

The formulations described herein are preferably low viscosity formulations having flow properties of readily flowing liquids at standard temperature and pressure, such as similar to the properties of water or milk. Optionally, the viscosity of the combined formulation is more viscous but still flowable at standard temperature and pressure, such as a viscosity similar to shampoo.

The formulations optionally contain one or more viscosity modifying agents.

In certain embodiments, the active agent formulations and/or combined formulations are free of thickeners or substantially free of thickeners (i.e. viscosity increasing agents). As used herein, "substantially free" refers to less than about 5%, 4%, 3%, 2%, or 1% of one or more thickeners present in the formulation. In certain embodiments, the active agent formulations described have less than about 1% of one or more thickeners present. Classes of thickeners include, but are not limited to, viscous liquids, such as polyethylene glycol, semisynthetic polymers, such as semisynthetic cellulose derivatives, synthetic polymers, such as carbomers, poloxamers, and polyethyleneimines (e.g., PEI-10), naturally occurring polymers, such as acacia, tragacanth, alginates (e.g., sodium alginate), carrageenan, alcohols, such as cetyl alcohol, vegetable gums, such as xanthan gum, petroleum jelly, waxes, particulate associate colloids, such as bentonite, colloidal silicon dioxide, and microcrystalline cellulose, surfactants, such as PPG-2 hydroxyethyl coco/isostearamide, emulsifiers, such as disteareth-75 IPDI, and salts, such as sodium chloride, and combinations thereof.

8. Antioxidants

The formulations may contain one or more antioxidants. Examples include, but are not limited to, tocopheryls, BHT, ascorbic acid, camellia sinensis leaf extract, ascorbyl palmitate, magnesium ascorbyl phosphate, carotenoids, resveratrol, triethyl citrate, arbutin, kojic acid, tetrahexydecyl ascorbate, superoxide dismutase, zinc, sodium metabisulfite, lycopene, ubiquinone, and combinations thereof.

9. Opacifying Agents

The formulations may contain one or more opacifying agents. Opacifying agents are added to the formulations to make them opaque. Suitable opacifying agents include, but are not limited to, glycol distearate and ethoxylated fatty alcohols.

C. Properties of the Active Agent Formulations

1. Creams

In certain embodiments, the active agent formulation may be in the form of a cream. The cream typically includes the active agent of Formulae I, II, or III in a suitable carrier. The cream may contain combinations of the active agents. The active agent may be included in any suitable concentration. Typical concentrations of the active agent in the cream range from small amounts such as approximately 0.05 wt % to about 25 wt % of the formulation, such as from about 0.1 wt % to about 10 wt %, from about 0.1 wt % to 4 wt %, or from about 0.5 wt % to 3 wt %. Typically, the active agent may be present in the formulation in an amount ranging from about 0.5 wt % to about 5 wt % of the formulation. Preferably the cream contains the active agent in a concentration ranging from 0.1% (wt) to 5% (wt), more preferably from 0.1% wt to 3% (wt). While greater concentrations of active agent could be present in the cream, they are generally not needed to achieve the desired results.

Additionally, the cream may include an oil, a hair conditioning agent, and/or a thickener. The cream may also include a fragrance, a plant extract, and/or a surfactant. The cream may be packaged in a tube, tub, bottle, or other suitable container.

When the active agent formulation in the form of a cream is combined with a hydroxide-containing agent formulation (e.g. mixed to form a combined formulation or applied simultaneously to the hair), a precipitate containing a metal ion is not formed.

2. Liquid Active Agent Formulations

In some embodiments, liquid active agent-containing formulations are provided, which are mixed at the time of use with a second formulation containing hydroxide-containing agents to provide a combined formulation for curling hair. In these embodiments, the liquid active agent formulation may contain any suitable concentration of active agent in a suitable carrier, typically a diluent, such as described above. The liquid active agent formulation may contain combinations of the active agents. The concentration of the active agent is suitable to provide a combined formulation with the appropriate final volume and final concentration of active agent, as desired.

For example, a liquid active agent formulation can contain a concentration of active agent ranging from about 0.05 wt % to about 25 wt % of the formulation, such as from about 0.1 wt % to about 10 wt %, from about 0.1 wt % to 4 wt %, or from about 0.5 wt % to 3 wt %. Typically, the active agent may be present in the formulation in an amount ranging from about 0.5 wt % to about 5 wt % of the formulation. In a preferred embodiment, the liquid active agent formulation contains about 5% (wt) to 20% (wt) active agent. Preferably the active agent-containing formulation is odorless.

a. Concentration of Active Agent

In some embodiments, a first active agent formulation, which may contain one or more active agents according to Formulae I, II, and/or III, is provided, which typically contains about 0.1 to about 50 wt % of one or more of the active agents described herein. The active agent formulation may contain from about 0.1 to about 30 wt %, from about 0.1 to about 20 wt %, from about 0.1 to about 10 wt %, from about 0.1 to about 10 wt %, or from about 0.5 to 5 wt % of one or more of the active agents described herein. The active agent formulations are typically in an aqueous solution and optionally include other suitable ingredients and/or excipients. The active agent formulations are preferably liquid active agent formulations. In some embodiments, the active agent formulations are preferably not in the form of a cream. The active agent formulations can be mixed with a hydroxide-containing agent formulation to form a combined formulation as described below.

In some embodiments, such as when the active agent is Bis-aminopropyl diglycol dimaleate, the active agent formulation may contain from about 0.1 to about 30 wt %, from about 0.1 to about 20 wt %, from about 0.1 to about 10 wt %, from about 0.1 to about 10 wt %, or from about 0.5 to 5 wt % of Bis-aminopropyl diglycol fimaleate. Optionally, the active agent formulation contains from about 0.5 to about 10 wt %, from about 1 to about 9 wt %, from about 2 to about 8 wt %, from about 2 to about 6 wt %, from about 2.5 to about 6 wt %, from about 3 to about 5.5 wt %, or from about 3 to about 5 wt % of Bis-aminopropyl diglycol dimaleate.

In some embodiments, such as when the active agent is maleic acid or a simple salt thereof, the active agent formulation may contain from about 0.1 to about 30 wt %, from about 0.1 to about 20 wt %, from about 0.1 to about 10 wt %, from about 0.1 to about 10 wt %, or from about 0.5 to 5 wt % of maleic acid or a simple salt thereof. Optionally, the active agent formulation contains from about 0.5 to about 10 wt %, from about 0.5 to about 9 wt %, from about 1 to about 8 wt %, from about 1 to about 7 wt %, from about 1 to about 6 wt %, from about 1 to about 3 wt %, or from about 1 to about 2 wt % of maleic acid or a simple salt thereof.

In certain embodiments, a second active agent formulation may be provided, which may be further applied to hair following a curling treatment as described herein. The second active agent formulation may contain the same active agent(s) as the first active agent formulation or may contain a different active agent(s) than the active agent(s) in the first active agent formulation. The second active agent formulation may contain the same concentration of the active agent or a different concentration of the active agent than the concentration of the active agent in the first active agent formulation. Second active agent formulations typically contain about 0.1 to 50 wt % of one or more of the active agents described herein. The active agent formulation may contain from about 0.1 to about 30 wt %, from about 0.1 to about 20 wt %, from about 0.1 to about 10 wt %, from about 0.1 to about 10 wt %, or from about 0.5 to 5 wt % of one or more of the active agents described herein.

The second active agent may be in the form of a liquid or a cream, optionally the second active agent is in an aqueous solution. Optionally, the second active agent formulation contains other suitable ingredients and/or excipients.

III. Hydroxide-Containing Formulations

As used herein, the term "hydroxide-containing formulations" refers to formulations that contain one or more hydroxide-containing agents. The hydroxide-containing formulation is preferably odorless.

The hydroxide-containing formulations do not contain a thiol based reducing agent, such as thioglycolic acid, thiolactic acid, thioglycerol, or mercaptopropionic acid, or salts thereof, thioglycerin or derivatives thereof. In certain other embodiments, the hydroxide formulations also do not contain other types of reducing agents, such as sodium bisuifite, ammonium bisulfide, clihycirolipoate. zinc formaldehyde sulfoxylate, sodium formaldehyde sulfoxylate, sodium metabisulfite, potassium borohydride, or pegylated thiols and/or hydroquinone.

Hydroxide-containing formulations and their methods of preparation are known in the art. In preferred embodiments the hydroxide-containing formulations are liquids, whereas non-preferred hydroxide-containing formulations which are commercially available, such as in the form of relaxing formulations from the following commercial brands: Mizani® Rhelaxer, Design Essentials®, and Dudley's Q®, are typically in the form of pastes.

Exemplary hydroxide-containing agents include, but are not limited, to alkali metal hydroxides such as sodium hydroxide, lithium hydroxide, and potassium hydroxide. In some other embodiments, the agent is ammonium hydroxide or guanidinium hydroxide. Hydroxide-containing agents are known to those of skill in the art.

In preferred embodiments, the hydroxide -containing formulations are free of any thiol-containing compounds or agents. Alternatively, the hydroxide-containing formulations are substantially free of any thiol-containing compounds or agents. As used herein, "substantially free" refers to a formulation that contains less than about 1 wt %, less than about 0.9 wt %, less than about 0.8 wt %, less than about 0.7 wt %, less than about 0.6 wt %, less than about 0.5 wt %, less than about 0.4 wt %, less than about 0.3 wt %, less than about 0.2 wt %, or less than about 0.1 wt % of any thiol-containing compound or agent.

IV. Combined Formulations Containing Active Agent(s) and Hydroxide-Containing Agent(s)

The term "combined formulation" as used herein refers to a formulation that contains both one or more hydroxide-containing agent(s) and one or more of the active agent(s) described above.

The combined formulation generally does not contain a nitrogen-containing base, such as guanadine, amidine, or a derivative thereof.

In some embodiments, separate active agent formulations and hydroxide containing formulations are provided, and are mixed at the time of use to provide a combined formulation.

In other embodiments, a combined formulation is provided (i.e. the active agent(s) and hydroxide-containing agent(s) are provided in a single formulation).

1. Concentrations

A combined formulation can contain a concentration of one or more hydroxide-containing agents of about 0.1 to 5% (wt), about 0.1 to 3% (wt), about 0.1 to 2% (wt), or about 0.1 to 1% (wt). In preferred embodiments, the concentration of one or more hydroxide-containing agents in the combined formulation is about 0.1 wt %, 0.2 wt %, 0.3 wt %, 0.4 wt %, 0.5 wt %, 0.6 wt %, 0.7 wt %, 0.8 wt %, 0.9 wt %, 1.0 wt %, 1.1 wt %, 1.2 wt %, 1.3 wt %, 1.4 wt %, or 1.5 wt %. The concentration of active agent in the combined formulation can range from about 0.5% (wt) to about 50% (wt) or greater. In certain embodiments, the combined formulation contains about 0.5% (wt) to 20% (wt) active agent. In certain embodiments, the combined formulation contains about 0.1 wt %, 0.2 wt %, 0.3 wt %, 0.4 wt %, 0.5 wt %, 0.6 wt %, 0.7 wt %, 0.8 wt %, 0.9 wt %, 1.0 wt %, 1.1 wt %, 1.2 wt %, 1.3 wt %, 1.4 wt %, 1.5 wt %, 1.6 wt %, 1.7 wt %, 1.8 wt %, 1.9 wt %, 2.0 wt %, 2.0 wt %, 2.1 wt %, 2.2 wt %, 2.3 wt %, 2.4 wt %, 2.5 wt %, 2.6 wt %, 2.7 wt %, 2.8 wt %, 2.9 wt %, or 3.0 wt %, or any concentration between the listed concentrations of the active agent(s).

In certain embodiments the combined formulations contain a molar excess of hydroxide-containing agent compared to the active agent(s) present having one or more acidic groups. In certain other embodiments the combined formulations are prepared based on the molar ratio of hydroxide-containing agent(s) to the number of acidic groups (i.e., carboxylic acid) present in the active agent(s) wherein the molar ratio can be about 2:1 or 1.5:1. In yet other embodiments, the molar ratio of hydroxide-containing agent(s) to the number of acidic groups (i.e., carboxylic acid) may be greater than or less than about 2:1 or 1.5:1 depending on the presence of one or more excipients and/or buffering agents, which can be acidic or basic, and may be present in the combined formulation.

2. Viscosity

The combined formulation may be in the form of a liquid. Preferably the viscosity of the liquid is less than the viscosity of a cosmetic cream, i.e. less than about 8,000 cP, optionally less than 5,000 cP.

Viscosity of the combined formulation can be determined according to known methods for measuring viscosity of fluids. In one non-limiting exemplary method, a Ford viscosity cup viscometer can be used to determine the viscosity of Newtonian fluids according to testing methods provided under ASTM D 1200-94. A Ford viscosity cup viscometer can also be used to determine the viscosity of non-Newtonian fluids according to testing methods provided under ASTM D 2196. Classical "Newtonian" fluids, as generally used herein, demonstrate a viscosity which is essentially independent of shear rate. "Non-Newtonian fluids," however, demonstrate a viscosity which either decreases or increases with increasing shear rate, e.g., the fluids are "shear thinning" or "shear thickening", respectively. These and other methods of measuring viscosity are described in Viswanath, et al. *Viscosity of Liquids: Theory, Estimation, Experiment, and Data,* Dordrecht:Springer, 2007, Print. Exemplary viscosities of fluids measured by a viscosity cup method (at 20° C.) in units of centipoise include water (1 cP), hand cream (8,000 cP), liquid soap (85 cP), and shampoo (3,000-5,000 cP).

Suitable viscosities for the combined formulations are in the range of about 1 to 3,000 cP, 1 to 2,000 cP, 1 to 1,000 cP, 1 to 750 cP, 1 to 500 cP, 1 to 250 cP, 1 to 100 cP, 1 to 90 cP, 1 to 80 cP, 1 to 70 cP, 1 to 60 cP, 1 to 50 cP, 1 to 40 cP, 1 to 30 cP, 1 to 20 cP, or 1 to 10 cP. In some embodiments, the combined formulations have a viscosity, as measured by a viscosity cup viscometer, which is within 1%, 2%, 3%, 4%, 5%, 6%, 7%, 8%, 9%, 10%, 20%, 30% of the viscosity of a reference fluid, such as water or shampoo, measured under the same conditions. In preferred embodiments, the combined formulation has a viscosity of less than 8,000 cP.

3. pH

In some embodiments, the pH of the combined formulation is about 11 or greater. In some embodiments, the pH of the combined formulation is about 10 or greater. In certain embodiments, the pH of the combined formulation is about 9.5 or greater, 9.6 or greater, 9.7 or greater, 9.8 or greater, 9.9 or greater, 10.0 or greater, 10.1 or greater, 10.2 or greater, 10.3 or greater, 10.4 or greater, 10.5 or greater, 10.6 or greater, 10.7 or greater, 10.8 or greater, 10.9 or greater, 11.0 or greater, 11.1 or greater, 11.2 or greater, 11.3 or greater, 11.4 or greater, 11.5 or greater, 11.6 or greater, 11.7 or greater, 11.8 or greater, 11.9 or greater, or 12.0 or greater. In certain other embodiments, the pH of the combined formulation is about 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, or 12.0.

4. Odorless

The combined formulation generally does not contain a foul smell. Preferably the combined formulation is odorless. However, perfumes may be included, if desired.

A. Combined Curling Formulations Formed by Mixing Immediately Prior to Application In some embodiments, combined formulations of a first active agent formulation and a second formulation containing hydroxide-containing agents are provided and these formulations are mixed at the time of use (such as in a salon by a stylist and/or colorist) wherein to provide a combined formulation for curling hair.

In certain embodiments of the combined formulations, the weight ratio of the one or more hydroxide-containing agents to the one or more active agents in the combined formulation can be in the range of about 10:1 to about 1:5; 5:1 to 1:5; 4:1 to 1:4; or 3:1 to 1:3. In some embodiments, the weight ratio of the one or more hydroxide-containing agents to the one or more active agents in the combined formulation is in the range of about 10:1 to about 1:1; 5:1 to 1:1; 4:1 to 1:1; or 3:1 to 1:1. In some instances, the weight ratio is about 10:1, 9:1, 8:1, 7:1, 6:1, 5:1, 4:1, 3:1, 2:1, 1:1, 1:2, 1:3, 1:4, or 1:5, preferably about 5:1, 4:1, 3:1, 2:1, 1:1, 1:2, 1:3, 1:4, or 1:5 or within about 10% of these ratios.

In such combined formulations, the amount of active agent(s) present does not lower the pH of the combined formulation to be below about a pH of 9.5 and more preferably does not lower the pH of the combined formulation below about a pH of 10.5.

B. Pre-Mixed Combined Curling Formulations

In some embodiments, combined formulations are provided, which contain both active agent(s) and hydroxide-containing agent(s). Such combined formulations can be sold as commercial formulations (to distributors and/or salons) as pre-mixed curling formulations containing both the active agent(s) and hydroxide-containing agent(s).

In some embodiments of the combined formulations, the weight ratio of the one or more hydroxide-containing agents to the one or more active agents in the combined formulation can be in the range of about 10:1 to about 1:5; 5:1 to 1:5; 4:1 to 1:4; or 3:1 to 1:3. In some embodiments, the weight ratio of the one or more hydroxide-containing agents to the one or more active agents is in the range of about 10:1 to about 1:1; 5:1 to 1:1; 4:1 to 1:1; or 3:1 to 1:1. In some instances, the weight ratio of the one or more hydroxide-containing agents to the one or more active agents in the combined formulation is about 10:1, 9:1, 8:1, 7:1, 6:1, 5:1, 4:1, 3:1, 2:1, 1:1, 1:2, 1:3, 1:4, or 1:5, and preferably about 5:1, 4:1, 3:1, 2:1, 1:1, 1:2, 1:3, 1:4, or 1:5, or within about 10% of these ratios.

Pre-mixed combined formulations can be prepared prior to use and sold as a commercial product to distributors and/or salons. The pre-mixed combined formulations can be stored and are shelf-stable. "Stable" of "slef-stable" as used herein with respect to shelf-life means that at least 40, 45, 50, 55, 60, 65, 70, 75, 80, 85, 90, or 95% of the active agent is not degraded over a specified time period, such as at least 6 months, at least 1 year, at least 2 years, at least 3 years after forming the combined formulation. Typically, the pre-mixed combined formulations are stored at room temperature optionally under light-free conditions.

V. Kits

In some embodiments, kits for curling hair contain an active agent formulation containing an active agent.

The kit may further contain a second formulation, also referred to herein as the hydroxide-containing formulation. The hydroxide-containing agent and active agent formulations are typically provided separately and instructions are provided for applying the hydroxide-containing agent and active agent formulations to the hair. For example, the instructions may provide for creating a combined formulation by mixing the hydroxide-containing agent and active agent formulations, and then applying the combined formulation to the hair. Alternatively, the instructions may provide for applying the hydroxide-containing agent to the hair simultaneously while applying the active agent formulation to the hair (but not as a pre-mixed, combined formulation).

The instructions may also include instructions for selecting the desired amount of active agent to be used, such as by specifying a volume or mass (or range thereof) of the active agent or active agent formulation, the desired weight ratio of active agent to hydroxide-containing agent, and/or the desired weight ratio of first hydroxide-containing formulation to second active agent formulation in order to control the level of curl imparted to the hair.

Alternatively, instructions are provided for first applying the hydroxide-containing agent to the hair and subsequently applying the active agent formulation to the hair. The instructions may specify the amount of time (i.e., in the range of about one second to about 30 minutes, more preferably within about 60 seconds) that can pass following the application of the hydroxide-containing formulation before the application of the active agent formulation and/or the amount of active agent formulation to be applied in order to control the level of curl imparted to the hair. The instructions may also specify how to select the desired amount of active agent to be used, such as by specifying a volume or mass (or range thereof) of the active agent or active agent formulation, the desired weight ratio of active agent to hydroxide-containing agent, and/or the desired weight ratio of a first hydroxide-containing formulation to a second active agent formulation in order to control the level of curl imparted to the hair being curled.

In other embodiments, the kits for curling hair contain a combined formulation. Instructions for use of the kit are also typically provided.

A. Hydroxide-Containing Formulation

In some embodiments, the kit contains hydroxide-containing agent(s) or a formulation thereof which contains one or more hydroxide-containing agents as described above. The hydroxide-containing formulation is typically provided in the form of a liquid in a container. The hydroxide-containing formulation included in the kit is preferably odorless. In some embodiments, the hydroxide-containing formulation may contain perfumes. Alternatively, the kit may further include perfumes which may be added to the hydroxide-containing formulation.

B. Active Agent Formulation

The active agent formulation contains one or more active agents as described herein. Suitable formulations containing the active agents are discussed above. The active agent formulation may be in any suitable form. Typically, the active agent formulation is a flowable liquid at standard temperature and pressure, such as a low to moderate viscosity liquid. The active agent formulation is provided in a suitable container, which depends on the form of the formulation.

In some embodiments, the active agent formulation is provided as two or more separate ingredients. For example, the active agent may be provided as a dry powder in a sealed package and the excipient(s) provided in a vial or other container. A suitable mixing container for the active agent and the excipient(s) may be provided.

The active agent formulation included in the kit is preferably odorless. In some embodiments, the active agent formulation may contain perfumes.

Alternatively, the kit may further include perfumes which may be added to the active agent formulation.

C. Combined Formulation

In some embodiments, the kit contains a pre-mixed combined formulation, which contain both the active agent(s) and the hydroxide-containing agent(s), as described above. The combined formulation is typically provided in the form of a liquid in a container. The combined formulation included in the kit is preferably odorless. In some embodiments, the combined formulation may contain perfumes. Alternatively, the kit may further include perfumes which may be added to the combined formulation.

VI. Methods of Use

Methods for curling hair are described herein. The curling methods can be used to impart curl to a variety of different types of hair, including but not limited to naturally straight hair, such as Asian hair, straight Hispanic hair, or straight Caucasian hair, wavy hair in general, and hair that was previously subjected to a relaxing treatment, colored, or bleached.

In some embodiments, the methods include controlling, selecting, or tuning the level of curl imparted during a hair curling process or treatment (using a hydroxide-containing formulation) by controlling the relative amount of an active agent formulation to the amount of hydroxide-containing agent formulation.

In some embodiments, the method for curling hair involves applying a first formulation to the hair containing one or more hydroxide-containing agents and applying a second formulation to the hair comprising one or more active agents of Formula I, II, and/or III, as described above. According to certain embodiments, the application of the first and second formulations is performed simultaneously. For example, the first and the second formulations are optionally mixed to form a combined formulation prior to application and the combined formulation is applied to the hair. For example when the hair to be curled is set as desired on a rod or curler, first one or more hydroxide-containing agents may be added to a formulation containing the active agent, or vice versa to form a single combined formulation and the combined formulation may be applied to the hair being curled.

Preferably when the first and second formulations are applied simultaneously as a combined formulation, the amount of active agent formulation present in the combined formulation does not lower the pH of the combined formulation to a pH below about 9.5, and more preferably does not lower the pH of the combined formulation to a pH below about 10.5. In other embodiments, when the first and second formulations are applied simultaneously, the amount of active agent formulation in the combined formulation results in a combined formulation with a pH of about 10 or greater, and more preferably a pH of about 11 or greater. In certain embodiments, the pH of the combined formulation is about 9.5 or greater, 9.6 or greater, 9.7 or greater, 9.8 or greater, 9.9 or greater, 10.0 or greater, 10.1 or greater, 10.2 or greater, 10.3 or greater, 10.4 or greater, 10.5 or greater, 10.6 or greater, 10.7 or greater, 10.8 or greater, 10.9 or greater, 11.0 or greater, 11.1 or greater, 11.2 or greater, 11.3 or greater, 11.4 or greater, 11.5 or greater, 11.6 or greater, 11.7 or greater, 11.8 or greater, 11.9 or greater, or 12.0 or greater. In certain other embodiments, the pH of the combined formulation is about 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, or 12.0.

In certain embodiments, the preferred low end of the pH range of the combined formulation depends on the type of hair being curled. In non-limiting examples, the pH of the combined formulation is preferably no less than about 12 when Asian hair is being curled. In another non-limiting example, the pH of the combined formulation is preferably no less than about 10 when Caucasian hair is being curled. In other non-limiting examples, the pH of the combined formulation is about 11 or greater when Asian hair is being curled. In another non-limiting example, the pH of the combined formulation is about 10 or greater when Caucasian hair is being curled.

Preferably the curling methods described are performed at room temperature and in the absence of any application of an external heat source during the curling method. In less preferable embodiments, heating may be applied, for example during the setting period after the hydroxide-containing and active agent formulations have been applied to the hair. Heating of the hair during the setting period is preferably kept below about 100° C., about 90° C., about 80° C., about 70° C., about 60° C., or about 50° C. Non-limiting examples of heat sources that may be used during the setting period include, but are not limited to, a hair dryer or salon hair dryer.

Following application of the first and second formulations or the combined formulation, the hair is rinsed after a setting period. Further optionally, subsequently, a second active agent formulation containing one or more active agents of Formula I, II, and/or III may be applied to the hair (which was previously treated in the first step).

In some embodiments, the method for curling hair involves applying a first formulation to the hair containing one or more hydroxide-containing agents and subsequently applying to the hair one or more active agents of Formula I, II, and/or III, as described above.

In still other embodiments, one or more of the active agents of the Formula I, II, and/or III, as described above, may be added to the formulation containing one or more hydroxide-containing agents prior to applying the formulation to the hair to form a combined formulation. Typically, the active agent(s) are added immediately prior to applying the combined formulation to the hair for the curling treatment.

The curling methods described herein curl hair; in contrast, applying to hair hydroxide-containing agent(s) alone would not be expected to produce any curl. Further the amount of the one or more active agents of the second formulation in combination with the first formulation are effective to impart a desired level of curl in the curled hair with reduced damage or breakage compared to treatments that do not include an active agent according to Formulation I, II, and/or III.

A. Reshaping the Hair

The methods described herein include the step of reshaping hair prior to, during, or following the application of any formulation containing one or more active agents and/or one or more hydroxide-containing agents.

Reshaping the hair typically includes using a tool, device or technique to place the hair in a particular shape, which is later removed or deconstructed, to achieve a desired hair style. For example, reshaping the hair can include rolling the hair on a roller, rod, and/or curler; or braiding or twisting the hair; or combinations thereof.

In some embodiments, reshaping the hair includes rolling the hair on or around a perm roller, curler, curling rod, or other suitable hair shaping instruments or tools prior to application of any formulation or combinations thereof. Reshaping of the hair can include braiding and/or twisting of the hair, optionally in combination with or in the absence of any roller, curler, curling rod, and/or other suitable hair shaping instrument.

Braided or twisted hair, for example, will then acquire curl as a result of the braiding or twisting of the hair. The hair may be braided or twisted as desired to tune the size and shape of the curl imparted following application of the curling methods described herein. In yet another instance, the hair may be braided or twisted, optionally in the absence of any roller, curler, curling rod, and/or other suitable hair shaping instrument, during the application of an active agent formulation, hydroxide-containing formulation, either simultaneously or as combined formulations thereof to the hair (i.e., wetting of the hair) as described herein. The braided or twisted hair will then acquire curl as a result of the braiding or twisting of the hair. The hair may be braided or twisted as desired to tune the size and shape of the curl imparted following application of the curling methods described herein.

In preferred embodiments, the hair is rolled (e.g. on curlers or rods), or is braided or twisted, prior to the application of the formulation(s) containing one or more hydroxide-containing agents and active agent(s).

In non-preferred embodiments, the hair may be rolled on curlers or rods, or is braided or twisted, after the application of the formulation(s) containing one or more hydroxide-containing agents and active agent(s). In these instances, the hair is preferably rolled, braided or twisted immediately after application of the formulations at least within about 1-15 minutes, more preferably about 1-10 minutes, and most preferably about 1-5 minutes.

B. Apply Formulation(s) Containing One or More Hydroxide-Containing Agents and Active Agent(s)

The active agent is applied to the hair either simultaneously with the hydroxide-containing agent (such as in the form of a combined formulation) or is applied immediately following the application of the hydroxide-containing formulation (wherein the hair has not been rinsed prior to application of the second formulation) or, alternatively, applied at a short interval of time immediately following the application of the hydroxide-containing formulation. "Short interval," as used herein, refers to a period of time in the range of one second to 30 minutes, one minute to 20 minutes, or 5 minutes to 15 minutes.

Preferably, the active agent is applied simultaneously with the one or more hydroxide-containing agent(s) to the hair during the reshaping method.

The active agent formulation may be applied as a single application, or application may be repeated one or more times as needed. Preferably, the amount of active agent formulation applied is sufficient to saturate the hair. The volume of active agent formulation applied to the hair in each application may be about 1 to about 200 mL depending on the length and volume of hair.

In certain other embodiments, a pre-mixed, combined formulation containing one or more hydroxide-containing agent(s) and a second formulation containing one or more active agent(s) is applied to the hair as part of a curling process.

In some embodiments, a first formulation containing one or more hydroxide-containing agent(s) and a second formulation containing one or more active agent(s) are mixed and applied to the hair as a single combined formulation containing both types of agents to the hair as part of a curling process. Alternatively, the first formulation and second formulation can be applied simultaneously to the hair without a prior mixing step.

When the formulations are applied simultaneously, the amount of active agent formulation used does not lower the pH of the combined formulation to be below about a pH of 10 and preferably does not lower the pH of the combined formulation below about a pH of 11 and the weight ratio of the hydroxide-containing agent formulation to the active agent formulation can be in the range of about 10:1 to about 1:5; 5:1 to 1:5; 4:1 to 1:4; or 3:1 to 1:3. In some embodiments, the weight ratio of the hydroxide-containing agent formulation to the active agent formulation is in the range of about 10:1 to about 1:1; 5:1 to 1:1; 4:1 to 1:1; or 3:1 to 1:1. In some instances, the weight ratio of the hydroxide-containing agent formulation to the active agent formulation is about 10:1, 9:1, 8:1, 7:1, 6:1, 5:1, 4:1, 3:1, 2:1, 1:1, 1:2, 1:3, 1:4, or 1:5, and preferably about 5:1, 4:1, 3:1, 2:1, 1:1, 1:2, 1:3, 1:4, or 1:5 or within about 10% of these ratios.

The amount of the second formulation containing active agent(s) and the concentration of the active agent(s) present therein can be varied as needed when using other hydroxide-containing agents to achieve similar results.

In non-preferred embodiments, commercially available formulations containing one or more hydroxide-containing agents, which typically have a pH of about 11 to 14, representing a difference in hydroxide ion concentration of about 100 times between the ends of the range may be used. In such instances, the amount of active agent(s) can be varied as a function of the pH of the commercially available relaxing formulation being used, and can be further adjusted according to the buffering capacity of each hydroxide-containing agent formulation, if a buffering agent is present.

In certain embodiments, the first and second formulations can be prepared at the time of use or immediately before as a single combined formulation containing both one or more hydroxide-containing agent(s) and the active agent(s) of Formulae I, II, and/or III having the weight ratios as described above.

In certain embodiments, the first and second formulation can be prepared as a single combined formulation, containing both the one or more hydroxide-containing agent(s) and the active agent(s) of Formulae I, II, and/or III having the weight ratios as described above and stored prior to use.

The single combined formulation typically has a pH in the range of 10 to 14, preferably a pH ranging from 11 to 13. According to certain embodiments, the single combined formulation contains about 0.1 to 10 wt % of one or more hydroxide-containing agent(s) and about 0.05 to 10 wt % of one or more active agents when prepared as a single aqueous solution or when a first and second formulation are prepared individually and subsequently mixed to form a single combined formulation.

Following application of the active agent and hydroxide-containing agent, the hair is allowed to set for a specified period of time, typically in the range of about 1 to 90 minutes, preferably about 10, 20, 30, or 40 minutes.

Preferably the method is performed at room temperature and in the absence of any application of an external heat source during the method. In less preferable embodiments, heat may be applied, for example, during the setting period after the hydroxide-containing and active agents have been applied to the hair. Heating of the hair is preferably kept below about 100° C., about 90° C., about 80° C., about 70° C., about 60° C., or about 50° C. Non-limiting examples of heat sources which may be used during the setting period include, but are not limited to, a hair dryer or salon hair dryer.

C. Removal of Formulations from Hair

Subsequently, the formulation containing one or more hydroxide-containing agents and the active agent formulation or combined formulations thereof applied to the hair are rinsed from the hair, typically the rinsing step lasts for a period of time in the range of about 0.1 to 10 minutes, preferably for about 1 to 5 minutes, more preferably about 3 to 5 minutes. If the hair is rinsed prior to removal from the curling rod, curler, or roller, or undoing of the braid and/or twist, then the rinsing time is preferably longer.

Optionally, the curled hair is removed from the rods/rollers/curlers or the braid or twist is undone, and the hair is then rinsed. However, this process generally takes a relatively long time. Therefore, it is generally useful when only a few rods, curlers, or rollers are placed in the hair. Optionally the hair may be immediately rinsed, shampooed and/or conditioned or subjected to one or more wash cycles and then allowed to dry (i.e., air drying, blotting, towel drying, blow drying). Rinsing can be performed with water at a temperature ranging from about room temperature (i.e., about 23-25° C.) to about 40° C.

The curled hair can be rinsed, shampooed, optionally conditioned, or subjected to one or more wash cycles subsequent to the curling process. The hair may be rinsed and subsequently shampooed, optionally conditioned, or subjected to one or more wash cycles immediately (e.g. within 10, 15, 25, 30, 45, 60 seconds (one minute), two minutes, three minutes, four, or five minutes following application) after application of the active agent formulation.

In some embodiments of the methods described herein, the curled hair is rinsed, shampooed, optionally conditioned, or subjected to one or more wash cycles about 45 minutes after the application of the formulations containing one or more hydroxide-containing agents and active agent(s), when they are applied simultaneously. In some embodiments of the methods described herein, the curled hair is rinsed, shampooed, optionally conditioned, or subjected to one or more wash cycles about 15 minutes after the application of an active agent formulation, when the active agent formulation is applied immediately (i.e., within about 5, 10, 15, 20, 25, 30, 35, 40, 45, 50, 55, 60 seconds (one minute), two minutes, three minutes, four, or five minutes) after applying the hydroxide-containing agent formulation.

Alternately, the hair may be rinsed, shampooed, optionally conditioned, or subjected to one or more wash cycles and a subsequent application of the active agent formulation may be applied which does not have to be rinsed, shampooed, optionally conditioned, or subjected to one or more wash cycles after application to the hair.

D. Optionally Apply a Second Active Agent Formulation to the Hair

Optionally, while the hair is still in the rollers/rods/curlers/braid/twist, a second active agent formulation which comprises one or more of the active agents of Formula I, II, and/or III may be applied to the treated hair.

The optional second active agent formulation, when applied, is allowed to sit in the hair for a period of time in the range of about 1 to 30 minutes, more preferably about 1 to 15 minutes.

The curled hair is then removed from the perm roller/curler/curling rod/braid/twist and can optionally be immediately shampooed, rinsed, optionally conditioned, or subjected to one or more wash cycles and then allowed to dry (i.e., air drying, blotting, towel drying, blow drying).

E. Properties of Curled Hair Following Curling Treatment

Treatment using the curling methods and formulations described herein can improve hair quality, such as appearance (e.g., sheen) and feel, increase wet and dry strength, and decrease hair breakage, even when the hair is subjected to subsequent styling treatments, such as coloring or bleaching, or additional curling or straightening treatments (such as to modify the curl, change the shape of the curl, or modify the level of curl (e.g. tighter or looser curls)).

1. Reduced Damage/Hair Breakage

Hair breakage is a significant problem encountered during typical hair curling treatments, such as permanent wave treatments. In the present embodiments, hair breakage can be decreased by using the curling methods described herein, as compared to standard curling treatments.

2. Retention of Curl

In certain embodiments, the curl imparted to the hair can be retained after at least about 1 to 30 wash cycles, preferably for at least about 1, 2, 3, 4, 5, 6, 7, 8, 9, 10, 20, 30, 40, or 50 wash cycles.

The amount and shape of the curl imparted is influenced by the size of the curling device or technique (e.g. curlers, rollers, rods, braids, or twists) used in combination with the application of the first and second formulations described herein.

The curl imparted to the hair following a curling treatment can be maintained with no appreciable or substantially no appreciable change for a period of time in the range of one week to six months, such as in the range of two weeks to four months or one month to three months. In some embodiments, the percentage of curl can be maintained for at least about one week, two weeks, three weeks, four weeks, one month, two months, three months, four months, five months, six months, or longer. The treated hair retains curl when subjected to conditions under which it would not retain the curl absent treatment according to the methods described herein, such as rinsing, shampooing, conditioning, or one or more wash cycles. "Wash cycles," as used herein refers to hair which has been subjected to the following: rinsing-shampooing-rinsing-conditioning-rinsing of the hair following a curling treatment described herein. Rinsing can be performed with water at a temperature ranging from about room temperature (i.e., about 23-25° C.) to about 40° C.

In some embodiments, the percentage of curl is reduced by less than about 5%, 10%, 15%, or 20% of the imparted curl after about 1, 2, 3, 4, 5, 6, 7, 8, 9, 10, 15, 20, 25, 30, 35, 40, 45, or 50 or more wash cycles. In yet other embodiments, the percentage of curl is reduced by less than about 30%, 40%, or 50% of the imparted curl after about 20-50 wash cycles. In certain embodiments, the imparted curl is retained with no appreciable or substantially no appreciable change after about 1, 2, 3, 4, 5, 6, 7, 8, 9, 10, 15, 20, 25, 30, 35, 40, 45, or 50 or more wash cycles, preferably two or more wash cycles, more preferably at least 5 wash cycles, more preferably after about 5-10 wash cycles.

As used herein, "percent change in the level of curl" and "percentage of change in curl" are used interchangeably to refer to the level of curl that is maintained over time (e.g. following one or more wash cycles) following a curling treatment. One non-limiting exemplary method for determining percent change in the level of curl in the hair (e.g. a swatch of hair) is based on the following formula:

$$\text{Percent Change in the level of Curl} = (L_F - L_i)/(L_i) \times 100$$

where $L_F$ is the final length of the hair following one or more wash cycles or a set period of time, and $L_i$ is the length of the curled hair following a curling treatment. For example, the level of curl (percent curl) following treatment with the active agent(s) and hydroxide-containing agent(s) can be maintained after washing with no significant loss in the curl, such the range of about 0-50%, for example less than about 40%, less than about 30%, less than about 20%, less than about 10%, less than about 5% change in the level of curl. The change in the level of curl can be determined after one or more wash cycles, with $L_F$ corresponding to the length of the curled hair after a particular number of wash cycles, such as after 1, 2, 3, 4, 5, 6, 7, 8, 9, 10, 15, 20, 25, 30, 35, 40, 45, or 50 or more wash cycles. Alternatively, the level of curl imparted following a curling method and the corresponding retention of curl after one or more wash cycles can be evaluated by visual inspection. Visual inspection is particularly useful when the hair being curled has natural curl or has been previously curled. Visual inspection is also useful to determine changes in the nature of curls, such as the shape and/or tightness of the curl.

F. Optional Subsequent Straightening or Curling Treatments to Modify the Level of Curl After performing the hair curling methods described herein, the level of curl can be modified by one or more additional curling treatments according to the same methods described herein. For example, the curling methods described may be applied repeatedly to hair in order to selectively modify the level of curl over a period of time, such as from day to day, week to week or month to month, or other suitable intervals of time. In non-limiting cases, the curling methods may be repeated 10, 20, 30, 40, 50, or more times at the aforementioned time intervals. Optionally, after using the hair curling methods described herein, the hair can be treated immediately thereafter (i.e. within 24 hours of the curling treatment) with a straightening process to straighten the hair. Further optionally, a subsequent curling method may be applied within 24 hours to curl the hair. This allows one to tune and modify the level of curl in hair, as desired, without damaging the hair.

EXAMPLES

Example 1

Curling of Asian Hair

Composition of Formulations 1 & 2:
Formulation 1 contained 2 wt % NaOH and 2 wt % Bis-Aminopropyl Diglycol Dimaleate with the remainder of the formulation being made up of water.
Formulation 2 contained 4 wt % Bis-Aminopropyl Diglycol Dimaleate with the remainder of the formulation being made up of water.
Curling Procedure:
Formulation 1 was prepared immediately prior to use and applied to a swatch of Asian hair in a perm roller and allowed to sit for 20 minutes. The hair sample was then thoroughly rinsed with room temperature water for 3 minutes and then blotted with a paper towel. Formulation 2 was added to the hair sample and allowed to sit for 20 minutes. The hair sample was then rinsed, removed from the roller, shampooed and conditioned and allowed to air dry.
Curling Results:
The hair retained a curl and exhibited a better condition, as compared to the hair prior to treatment, such as increased smoothness and shine.
Curl retention was tested after 20 wash cycles including shampooing and conditioning. After the 20 wash cycles, the curl retention was nearly identical to the curl after the initial treatment.

Example 2

Curling of Asian Hair

Composition of Formulations 1 & 2:
Formulation 1 contained 2 wt % NaOH with the remainder of the formulation being made up of water.
Formulation 2 contained 4 wt % Bis-Aminopropyl Diglycol Dimaleate with the remainder of the formulation being made up of water.
Curling Procedure:
Two swatches of Asian hair were rolled into perm rollers and each swatch was treated with Formulation 1 for 20 minutes. Both hair swatches were then rinsed for 3 minutes and blotted with a paper towel. One of the swatches was then treated with Formulation 2 for 20 minutes and the other swatch was treated with a 5 wt % acetic acid aqueous solution for 20 minutes. Both swatches were then rinsed, removed from the perm rollers, shampooed and conditioned and allowed to air dry.
Curling Results:
The hair swatch neutralized with Formulation 2 demonstrated curl retention but was in worse condition than prior to the treatment and in significantly inferior condition, when compared to the swatch treated according to the conditions listed in Example 1 (above).
The sample neutralized with the acetic acid solution did not hold a curl and was significantly damaged and in a worse state than the swatch neutralized by Formulation 2.

Example 3

Curling of Caucasian Hair

Composition of Formulations 1 & 2:
Formulation 1 contained 2 wt % NaOH and 4 wt % Bis-Aminopropyl Diglycol Dimaleate with the remainder of the formulation being made up of water.
Formulation 2 contained 4 wt % Bis-Aminopropyl Diglycol Dimaleate with the remainder of the formulation being made up of water.
Curling Procedure:
Formulation 1 prepared immediately prior to use and applied to Caucasian hair in a perm roller and allowed to sit for 20 minutes. The hair sample was then thoroughly rinsed in room temperature water for 3 minutes and blotted with a paper towel. Formulation 2 was added to the hair sample and allowed to sit for 20 minutes. The hair sample was then rinsed, removed from the perm roller, shampooed and conditioned and allowed to air dry.
Curling Results:
The treated hair retained curl and exhibited a better condition, as compared to the hair prior to treatment, such as increased smoothness and shine. Curl retention was tested after 10 wash cycles including shampooing and conditioning. After the 10 wash cycles, the curl retention was nearly identical to the curl after the initial treatment.

Example 4

Curling of Caucasian Hair

Composition of Formulations 1 & 2:
Formulation 1 contained 2.6 wt % NaOH and 4 wt % Bis-Aminopropyl Diglycol Dimaleate with the remainder of the formulation being made up of water.
Formulation 2 contained 3 wt % Bis-Aminopropyl Diglycol Dimaleate with the remainder of the formulation being made up of water and was in the form of cream.
Curling Procedure:
Formulation 1 was prepared immediately prior to use and applied to Caucasian hair in a perm roller and allowed to sit for 40 minutes. The hair sample was then thoroughly rinsed in room temperature water for 3 minutes and blotted with a paper towel. Formulation 2 was applied to the hair sample and allowed to sit for 10 minutes. The hair sample was then rinsed, removed from the perm roller, shampooed and conditioned and let air dry.

Curling Results:

The treated hair retained curl and exhibited a better condition, as compared to the hair prior to treatment, such as increased smoothness and shine. Curl retention was tested after 10 wash cycles including shampooing and conditioning. After the 10 wash cycles, the curl retention was nearly identical to the curl after the initial treatment.

Example 5

Curling of Asian Hair

Composition of Formulations 1 & 2:

Formulation 1 contained 2.6 wt % NaOH and 2 wt % Bis-Aminopropyl Diglycol Dimaleate with the remainder of the formulation being made up of water.

Formulation 2 contained 3 wt % Bis-Aminopropyl Diglycol Dimaleate with the remainder of the formulation being made up of water and was in the form of cream.

Curling Procedure:

Formulation 1 was prepared immediately prior to use and applied to Asian hair in a perm roller and allowed to sit for 40 minutes. The hair sample was then thoroughly rinsed in room temperature water for 3 minutes and blotted with a paper towel. Formulation 2 was applied to the hair and allowed to sit for 10 min. The hair sample was then rinsed, removed from the roller, shampooed and conditioned and let air dry.

Curling Results:

The treated hair retained curl and exhibited a better condition, as compared to the hair prior to treatment, such as increased smoothness and shine. Curl retention was tested after 10 wash cycles including shampooing and conditioning. After the 10 wash cycles, the curl retention was nearly identical to the curl after the initial treatment.

Example 6

Curling of Caucasian Hair

Composition of Formulation 1:

Formulation 1 contained 6.6 wt % NaOH and 1.25 wt % Bis-Aminopropyl Diglycol Dimaleate with the remainder of the formulation being made up of water.

Curling Procedure:

Formulation 1 was prepared immediately prior to use and applied to Caucasian hair in a perm roller and allowed to sit for 40 minutes. The hair sample was then rinsed, removed from the perm roller, shampooed and conditioned and let air dry.

Curling Results:

The treated hair retained a curl and exhibited a better condition, as compared to the hair prior to treatment, such as increased smoothness and shine. Curl retention was tested after 10 wash cycles including shampooing and conditioning. After the 10 wash cycles, the curl retention was nearly identical to the curl after the initial treatment.

Example 7

Curling of Asian Hair

Composition of Formulation 1:

Formulation 1 contained 6.6 wt % NaOH and 0.77 wt % Maleic Acid with the remainder of the formulation being made up of water.

Curling Procedure:

Formulation 1 was prepared immediately prior to use and applied to Asian hair in a perm roller and allowed to sit for 30 minutes. The hair sample was then rinsed, removed from the roller, shampooed and conditioned and let air dry.

Curling Results:

The treated hair retained a curl and exhibited a better condition, as compared to the hair prior to treatment, such as increased smoothness and shine. Curl retention was tested after 10 wash cycles including shampooing and conditioning. After the 10 wash cycles, the curl retention was nearly identical to the curl after the initial treatment.

Example 8

Curling of Caucasian Hair

Composition of Formulation 1:

Formulation 1 contained 6.6 wt % NaOH and 0.77 wt % Maleic Acid with the remainder of the formulation being made up of water.

Curling Procedure:

Formulation 1 was prepared immediately prior to use and applied to Asian hair in a perm roller and allowed to sit for 30 minutes. The hair sample was then rinsed, removed from the roller, shampooed and conditioned and let air dry.

Curling Results:

The treated hair retained a curl and exhibited a better condition, as compared to the hair prior to treatment, such as increased smoothness and shine. Curl retention was tested after 10 wash cycles including shampooing and conditioning. After the 10 wash cycles, the curl retention was nearly identical to the curl after the initial treatment.

Example 9

Curling of Caucasian Hair

Composition of Formulation 1:

Formulation 1 contained 6.6 wt % NaOH and 0.7 wt % Methacrylic Acid with the remainder of the formulation being made up of water.

Curling Procedure:

Formulation 1 was prepared immediately prior to use and applied to Asian hair in a perm roller and allowed to sit for 30 minutes. The hair sample was then rinsed, removed from the roller, shampooed and conditioned and let air dry.

Curling Results:

The treated hair retained a curl and exhibited a better condition, as compared to the hair prior to treatment, such as increased smoothness and shine. Curl retention was tested after 10 wash cycles including shampooing and conditioning. After the 10 wash cycles, the curl retention was nearly identical to the curl after the initial treatment.

Example 10

Curling of Caucasian Hair

Composition of Formulation 1:

Formulation 1 contained 6.6 wt % NaOH and 0.7 wt % Methacrylic Acid with the remainder of the formulation being made up of water.

Curling Procedure:

Formulation 1 was prepared immediately prior to use and applied to Asian hair in a perm roller and allowed to sit for 30 minutes. The hair sample was then rinsed, removed from the roller, shampooed and conditioned and let air dry.

Curling Results:

The treated hair retained a curl and exhibited a better condition, as compared to the hair prior to treatment, such as increased smoothness and shine. Curl retention was tested after 10 wash cycles including shampooing and conditioning. After the 10 wash cycles, the curl retention was nearly identical to the curl after the initial treatment.

Example 11

Curling of Caucasian Hair without Active Agent

Composition of Formulation 1:

Formulation 1 contained 6.6 wt % NaOH and 0.7 wt % Lactic Acid with the remainder of the formulation being made up of water.

Curling Procedure:

Formulation 1 was prepared immediately prior to use and applied to Asian hair in a perm roller and allowed to sit for 30 minutes. The hair sample was then rinsed, removed from the roller, shampooed and conditioned and let air dry.

Curling Results:

The treated hair did not retain any significant curl after 1 wash and after 3 wash cycles had less curl than before the treatment. The condition, as compared to the hair prior to treatment, was flat with increased frizz, breakage, and poor feel.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A method comprising:
   (a) applying to hair a formulation comprising one or more hydroxide-containing agents and an active agent of Formula II:

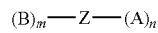

Formula II wherein Z is a linker or is absent and the linker is not a polymer; m and n are each an integer independently selected from 1-6, and the sum of m+n is equal to or greater than 2;
   B is a functional group capable of forming a covalent bond with a nucleophile and B is independently selected from the group consisting of:

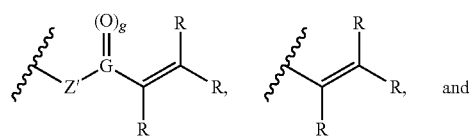

and

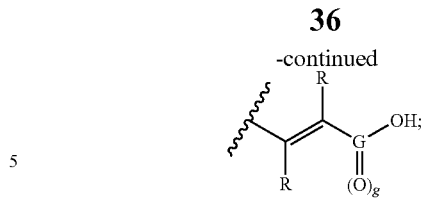

wherein each R is independently selected from the group consisting of hydrogen, $C_{1-6}$ alkyl groups, aryl groups, and ionizable functional groups and Z' is oxygen (O), NH or is absent, and G is carbon (C) and g is 1, or G is sulfur (S) and g is 2;
   A is an ionizable functional group independently selected from the group consisting of carboxylic acids, sulfonic acids, phosphonic acids, and amines;
   wherein the formulation has a pH of 10 or greater, and
   (b) reshaping the hair;
   wherein the method is substantially free of a sulfur-containing reducing agent; and
   wherein steps (a) and (b) are not followed by an oxidizing step.

2. The method of claim 1, wherein following steps (a) and (b), the hair retains curl when subjected to one or more wash cycles.

3. The method of claim 2, wherein the curl is retained for at least about 2, 3, 4, 5, 6, 7, 8, 9, 10, 15, 20, 25, 30, 35, 40, 45, or 50 wash cycles.

4. The method of claim 1, wherein step (b) occurs prior to step (a).

5. The method of claim 4, wherein the formulation is a combined formulation, and wherein prior to step (a), a first formulation comprising the one or more hydroxide-containing agents and a second formulation comprising the active agent of Formula II, are mixed to form the combined formulation.

6. The method of claim 1, wherein the one or more hydroxide-containing agents and active agent are in a weight ratio in the range of about 5:1 to 1:5.

7. The method of claim 1, wherein the one or more hydroxide-containing agents are selected from the group consisting of sodium hydroxide, lithium hydroxide, potassium hydroxide, guanidinium hydroxide, and ammonium hydroxide.

8. The method of claim 1, wherein the active agent is present in an amount ranging from about 0.5 wt % to about 20 wt % of the formulation.

9. The method of claim 1, wherein the step of reshaping the hair comprises (i) rolling the hair on a roller, rod, or curler, or a combination thereof; or (ii) braiding or twisting the hair; or a combination of (i) and (ii).

10. The method of claim 1, further comprising:
    (c) applying to the hair a second active agent formulation comprising a second active agent, wherein the second active agent is maleic acid or a simple salt thereof, acrylic acid or a simple salt thereof, methyl acrylic acid or a simple salt thereof, vinyl sulfonic acid or a simple salt thereof,

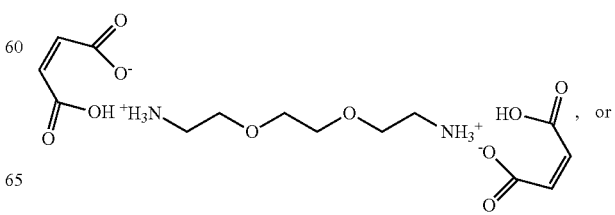

-continued

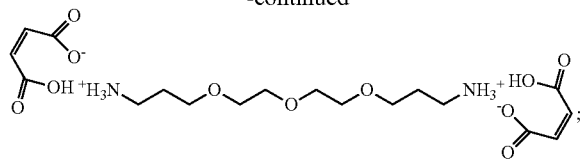

or a mixture thereof;
wherein step (c) occurs subsequent to step (b).

11. The method of claim 10, wherein the second active agent formulation comprises about 0.1 wt % to about 5 wt % of the second active agent.

12. The method of claim 10, wherein the second active agent is selected from the group consisting of maleic acid, acrylic acid, methyl acrylic acid, and vinyl sulfonic acid, and simple salts thereof.

13. The method of claim 1, wherein the formulation has a pH of 10.5 or greater.

14. A method comprising:
(a) applying to hair a formulation comprising one or more hydroxide-containing agents and an active agent of Formula II:

$$(B)_m\text{---}Z\text{---}(A)_n \quad \text{Formula II}$$

wherein Z is a linker or is absent and the linker is not a polymer; m and n are each an integer independently selected from 1-6, and the sum of m+n is equal to or greater than 2;
B is a functional group capable of forming a covalent bond with a nucleophile and B is independently selected from the group consisting of:

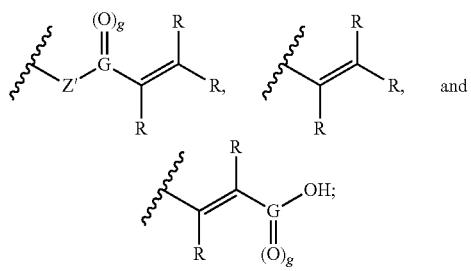

wherein each R is independently selected from the group consisting of hydrogen, $C_{1-6}$ alkyl groups, aryl groups, and ionizable functional groups and Z' is oxygen (O), NH or is absent, and G is carbon (C) and g is 1, or G is sulfur (S) and g is 2;
A is an ionizable functional group independently selected from the group consisting of carboxylic acids, sulfonic acids, phosphonic acids, and amines;
wherein the formulation has a pH of 10 or greater, and
(b) reshaping the hair;
wherein the method is substantially free of a sulfur-containing reducing agent; and
wherein the method does not include an oxidizing step.

15. The method of claim 14, wherein following steps (a) and (b), the hair retains curl when subjected to one or more wash cycles.

16. The method of claim 14, wherein the formulation is a combined formulation, and wherein prior to step (a), a first formulation comprising the one or more hydroxide-containing agents and a second formulation comprising the active agent of Formula II, are mixed to form the combined formulation.

17. The method of claim 14, wherein the one or more hydroxide-containing agents and active agent are in a weight ratio in the range of about 5:1 to 1:5.

18. The method of claim 14, wherein the one or more hydroxide-containing agents are selected from the group consisting of sodium hydroxide, lithium hydroxide, potassium hydroxide, guanidinium hydroxide, and ammonium hydroxide.

19. The method of claim 14, wherein the active agent is present in an amount ranging from about 0.5 wt % to about 20 wt % of the formulation.

20. The method of claim 14, wherein the step of reshaping the hair comprises (i) rolling the hair on a roller, rod, or curler, or a combination thereof; or (ii) braiding or twisting the hair; or a combination of (i) and (ii).

21. The method of claim 14, further comprising:
(c) applying to the hair a second active agent formulation comprising a second active agent, wherein the second active agent is maleic acid or a simple salt thereof, acrylic acid or a simple salt thereof, methyl acrylic acid or a simple salt thereof, vinyl sulfonic acid or a simple salt thereof,

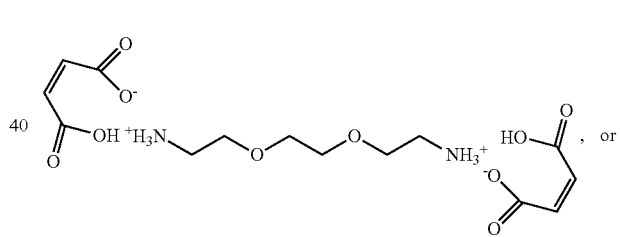

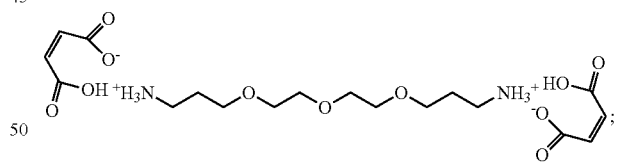

or a mixture thereof;
wherein step (c) occurs subsequent to step (b).

22. The method of claim 14, wherein the formulation has a pH of 10.5 or greater.

* * * * *

UNITED STATES PATENT AND TRADEMARK OFFICE
CERTIFICATE OF CORRECTION

PATENT NO. : 10,792,233 B2  
APPLICATION NO. : 15/855719  
DATED : October 6, 2020  
INVENTOR(S) : Eric D. Pressly and Craig J. Hawker Page 1 of 8

It is certified that error appears in the above-identified patent and that said Letters Patent is hereby corrected as shown below:

In the Specification

Column 7, Line 12, replace "aminoacid" with --amino acid--.
Column 10, Lines 41-49, replace structure:

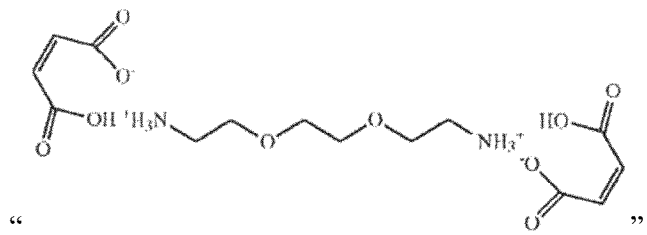
" "

With the following structure:

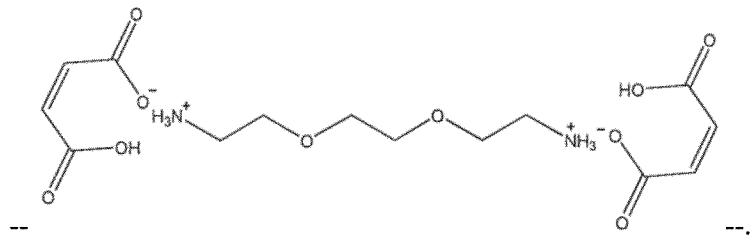
-- --.

Column 10, Lines 50-57, replace structure:

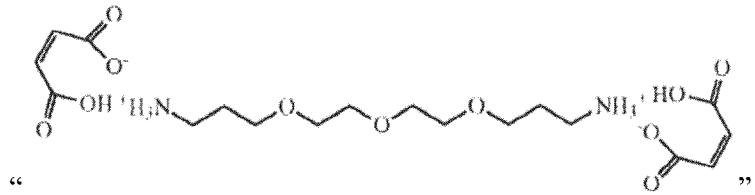
" "

With the following structure:

Signed and Sealed this  
Twenty-ninth Day of December, 2020

Andrei Iancu  
*Director of the United States Patent and Trademark Office*

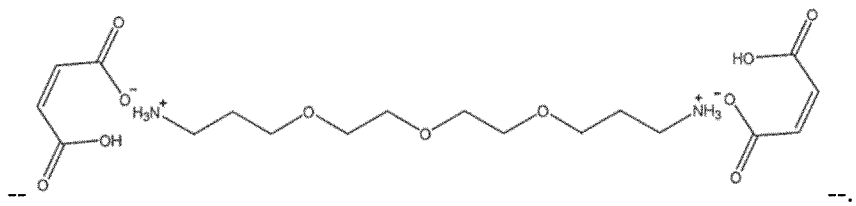
Column 11, Lines 25-30, replace structure:
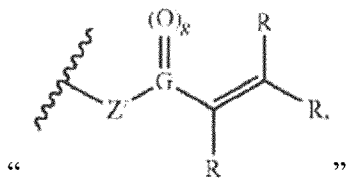
" "
With the following structure:
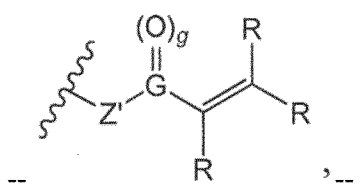
-- , --.
Column 11, Lines 30-35, replace structure:
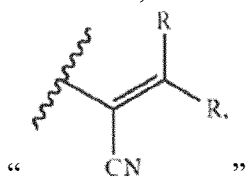
" "
With the following structure:
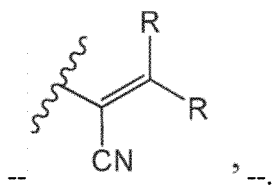
-- , --.
Column 11, Lines 30-35, replace structure:
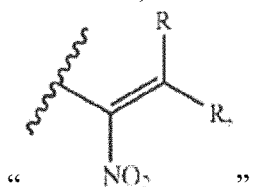
" "
With the following structure:
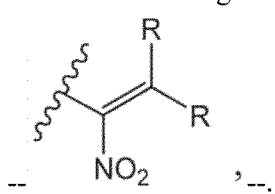
-- , --.
Column 11, Lines 36-41, replace structure:

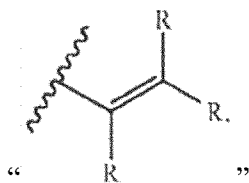
With the following structure:
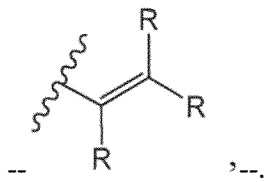
Column 11, Lines 50-57, replace structure:
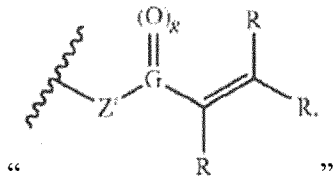
With the following structure:
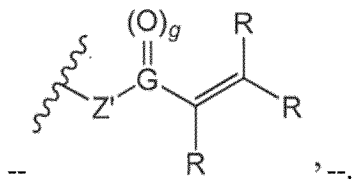
Column 11, Lines 50-57, replace structure:
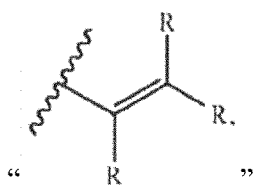
With the following structure:
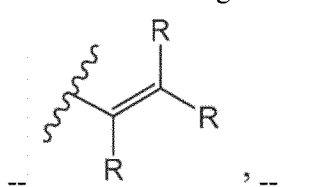
Column 13, Line 58, replace "not limited, to" with --not limited to,--.
Column 13, Lines 60-67, replace structure:
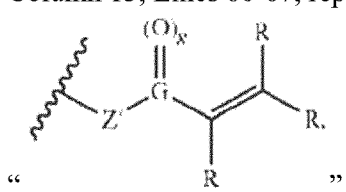
With the following structure:

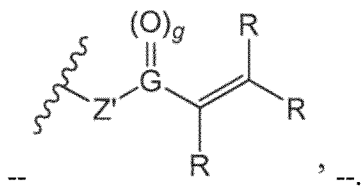
Column 14, Lines 1-8, replace structure:
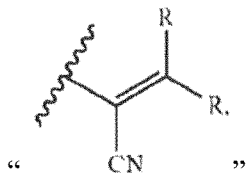
" CN "
With the following structure:
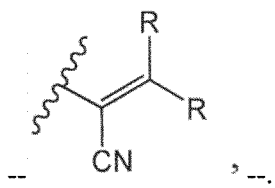
-- CN , --.
Column 14, Lines 1-8, replace structure:
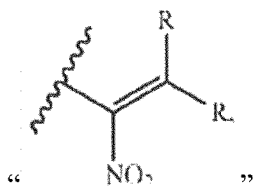
" NO₂ "
With the following structure:
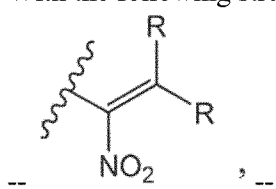
-- NO₂ , --.
Column 14, Lines 9-14, replace structure:
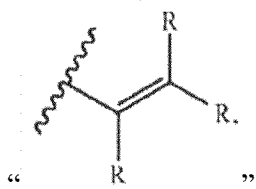
" R "
With the following structure:
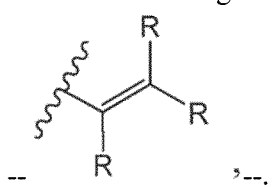
-- R , --.
Column 14, Lines 23-30, replace structure:

CERTIFICATE OF CORRECTION (continued)
U.S. Pat. No. 10,792,233 B2

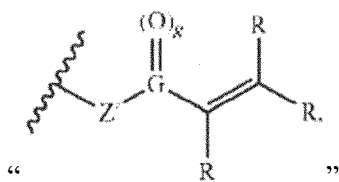

"

With the following structure:

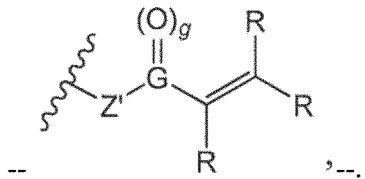

--                  ,--.

Column 14, Lines 23-30, replace structure:

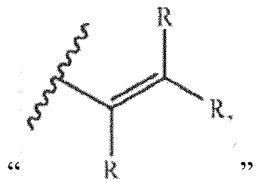

"

With the following structure:

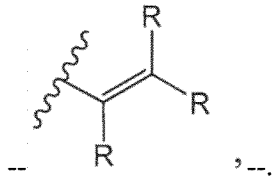

--            ,--.

Column 16, Lines 59-60, replace "N-dodecyl-.beta.-alanine" with --N-dodecyl-β-alanine--.
Column 19, Lines 61-62, replace "from about 0.1 to about 10 wt %, from about 0.1 to about 10 wt %" with --from about 0.1 to about 10 wt %--.
Column 20, Lines 8-9, replace "from about 0.1 to about 10 wt %, from about 0.1 to about 10 wt %" with --from about 0.1 to about 10 wt %--.
Column 20, Line 10, replace "Bis-aminopropyl diglycol fimaleate" with
--Bis-aminopropyl diglycol dimaleate--.
Column 20, Lines 19-20, replace "from about 0.1 to about 10 wt %, from about0.1 to about 10 wt %" with --from about 0.1 to about 10 wt %--.
Column 20, Lines 41-42, replace "from about 0.1 to about 10 wt %, from about 0.1 to about 10 wt %" with --from about 0.1 to about 10 wt %--.
Column 20, Line 55, replace "or mercaptopropionic acid" with --mercaptopropionic acid--.
Column 21, Line 5, replace "not limited, to" with --not limited to,--.
Column 24, Line 64, replace "contain" with --contains--.
Column 28, Line 29, replace "first and second formulation" with --first and second formulations--.

In the Claims

Claim 1, Column 35, Lines 61-67, replace structure:
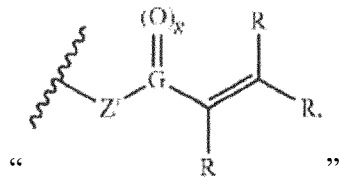
" "
With the following structure:
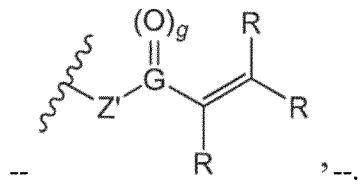
--   ,--.
Claim 1, Column 35, Lines 61-67, replace structure:
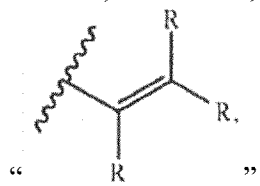
" "
With the following structure:
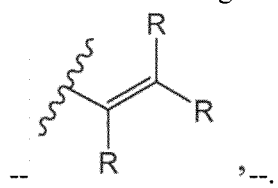
--   ,--.
Claim 10, Column 36, Lines 58-67, replace structure:
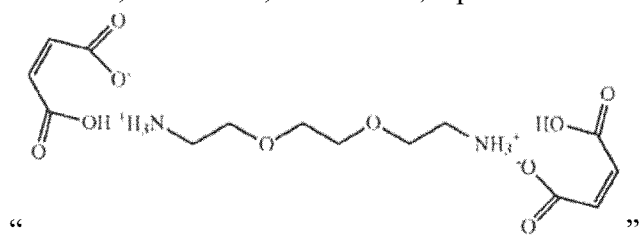
" "
With the following structure:
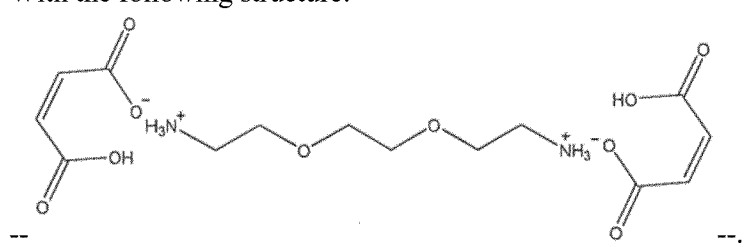
--   --.
Claim 10, Column 37, Lines 2-7, replace structure:

CERTIFICATE OF CORRECTION (continued)
U.S. Pat. No. 10,792,233 B2

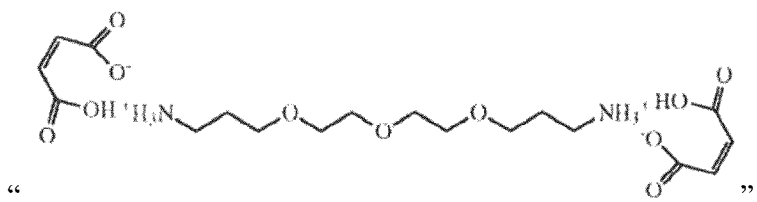

"

With the following structure:

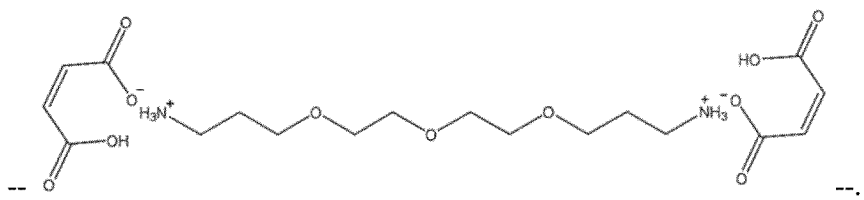

--.

Claim 14, Column 37, Lines 35-40, replace structure:

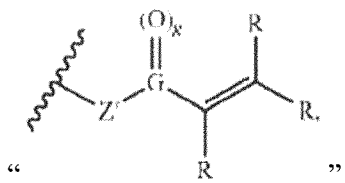

"

With the following structure:

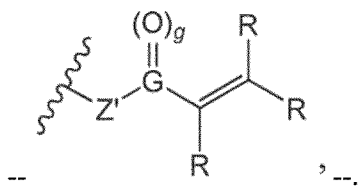

--.

Claim 14, Column 37, Lines 35-40, replace structure:

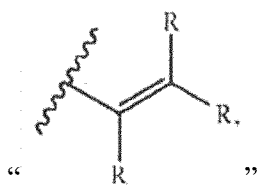

"

With the following structure:

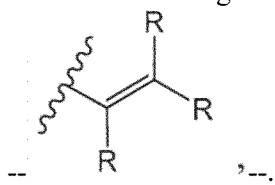

--.

Claim 21, Column 38, Lines 35-44, replace structure:

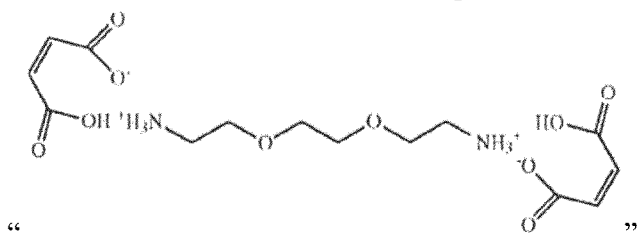

"

With the following structure:

CERTIFICATE OF CORRECTION (continued)
U.S. Pat. No. 10,792,233 B2

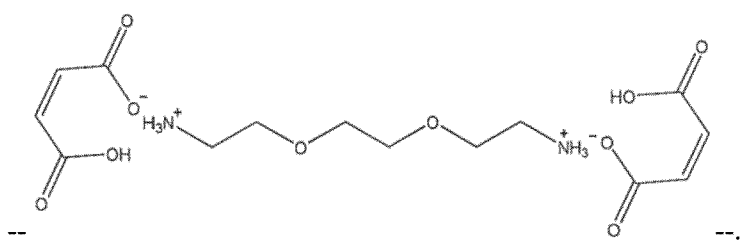

--                                             --.

Claim 21, Column 38, Lines 45-52, replace structure:

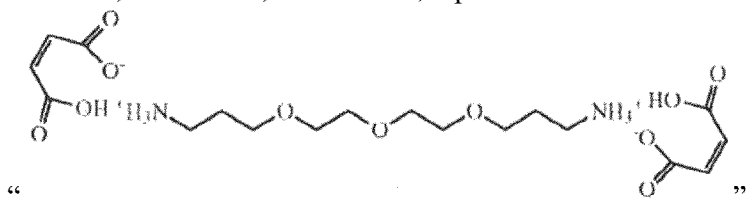

"                                             "

With the following structure:

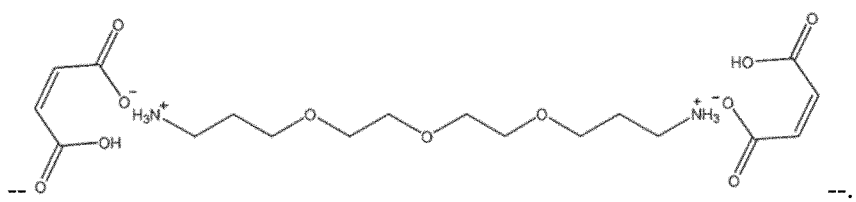

--                                             --.